(12) United States Patent
Yoshida et al.

(10) Patent No.: US 8,710,005 B2
(45) Date of Patent: *Apr. 29, 2014

(54) NEURONAL DIFFERENTIATION-INDUCING PEPTIDE AND USE THEREOF

(75) Inventors: Tetsuhiko Yoshida, Tsukuba (JP); Nahoko Kobayashi, Tsukuba (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/258,788

(22) PCT Filed: Apr. 12, 2010

(86) PCT No.: PCT/JP2010/056510
§ 371 (c)(1),
(2), (4) Date: Sep. 22, 2011

(87) PCT Pub. No.: WO2010/117079
PCT Pub. Date: Oct. 14, 2010

(65) Prior Publication Data
US 2012/0035112 A1    Feb. 9, 2012

(30) Foreign Application Priority Data
Apr. 10, 2009  (JP) .................................. 2009-095641

(51) Int. Cl.
*A61K 38/16* (2006.01)
*C07K 14/435* (2006.01)

(52) U.S. Cl.
USPC ........... 514/8.3; 514/17.7; 514/21.3; 530/300

(58) Field of Classification Search
None
See application file for complete search history.

(56) References Cited

U.S. PATENT DOCUMENTS

| | | | |
|---|---|---|---|
| 4,867,975 | A | 9/1989 | Gelb, Jr. |
| 6,037,521 | A | 3/2000 | Sato et al. |
| 6,340,583 | B1 | 1/2002 | Yan et al. |
| 6,403,353 | B1 | 6/2002 | Yan et al. |
| 6,423,684 | B1 | 7/2002 | Mochly-Rosen et al. |
| 2003/0125242 | A1 | 7/2003 | Rosenecker et al. |
| 2003/0166215 | A1 | 9/2003 | Yan et al. |
| 2003/0229202 | A1 | 12/2003 | Guo et al. |
| 2004/0175751 | A1 | 9/2004 | Yan et al. |
| 2004/0186052 | A1* | 9/2004 | Iyer et al. .................... 514/12 |
| 2004/0226056 | A1* | 11/2004 | Roch et al. .................. 800/12 |
| 2006/0100134 | A1 | 5/2006 | Guo et al. |
| 2006/0166917 | A1 | 7/2006 | Lindeman et al. |
| 2006/0270834 | A1 | 11/2006 | Kanno |
| 2007/0065941 | A1 | 3/2007 | Kondo et al. |
| 2008/0076145 | A1 | 3/2008 | Cummings et al. |
| 2009/0253618 | A1 | 10/2009 | Kanno et al. |
| 2010/0297758 | A1* | 11/2010 | Yoshida et al. ............... 435/366 |
| 2012/0122210 | A1 | 5/2012 | Yoshida et al. |
| 2012/0122225 | A1 | 5/2012 | Kobayashi et al. |
| 2012/0208752 | A1 | 8/2012 | Yoshida et al. |
| 2013/0005034 | A1 | 1/2013 | Yoshida et al. |
| 2013/0079273 | A1 | 3/2013 | Yoshida et al. |

FOREIGN PATENT DOCUMENTS

| | | |
|---|---|---|
| EP | 1 918 297 A1 | 5/2008 |
| JP | A-7-132033 | 5/1995 |
| JP | A-9-323928 | 12/1997 |
| JP | A-2001-199997 | 7/2001 |
| JP | A-2003-137899 | 5/2003 |
| JP | A-2004-357543 | 12/2004 |
| JP | A-2005-154338 | 6/2005 |
| JP | A-2005-330206 | 12/2005 |
| JP | B2-3854995 | 12/2006 |
| JP | A-2007-145761 | 6/2007 |
| JP | A-2007-159429 | 6/2007 |
| JP | A-2009-209064 | 9/2009 |
| JP | A-2011-016763 | 1/2011 |
| WO | WO 02/18572 A2 | 3/2002 |
| WO | WO 02/077171 A2 | 10/2002 |
| WO | WO 03/076561 A2 | 9/2003 |
| WO | WO 2004/056854 A1 | 7/2004 |
| WO | WO 2005/086800 A2 | 9/2005 |
| WO | WO 2007/010989 A1 | 1/2007 |
| WO | WO 2007/149293 A2 | 12/2007 |
| WO | WO 2008/008569 A2 | 1/2008 |
| WO | WO 2009/093692 A1 | 7/2009 |
| WO | WO 2010/117078 A1 | 10/2010 |
| WO | WO 2010/117079 A1 | 10/2010 |

OTHER PUBLICATIONS

Kwak YD et al. Amyloid precursor protein regulates differentiation of human neural stem cells. Stem Cells Dev. 2006, 15(3):381-389.*
Marutle A et al. Modulation of human neural stem cell differentiation in Alzheimer (APP23) transgenic mice by phenserine. Proc. Natl. Acad. USA, 2007, 104(30):12506-12511.*
Sugaya K et al. Practical issues in stem cell therapy for Alzheimer's disease. Curr. Alzheimer Res. 2007, 4(4):370-377; Abstract only.*
Khandekar N et al. (2012) Amyloid precursor proteins, neural differentiatioin of pluripotent stem cells and its relevance to Alzheimer's disease. Stem Cells Dev. 21(7):997-1006.*
Martoglio et al., "Signal sequences: more than just greasy peptides", Trends in Cell Biology Oct. 1998, pp. 410-415, vol. 8.
Kang et al., "The precursor of Alzheimer's disease amyloid A4 protein resembles a cell-surface receptor", Nature, Feb. 19, 1987, pp. 733-736, vol. 325.
Goyal et al., "Phosphorylation-dependent Regulation of Unique Nuclear and Nucleolar Localization Signals of LIM Kinase 2 in Endothelial Cells", Journal of Biological Chemistry, Sep. 1, 2006, pp. 25223-25230, vol. 281, No. 35.
Alexander et al., "The Role of Suppressors of Cytokine Signaling (SOCS) Proteins in Regulation of the Immune Response," Annu. Rev. Immunol., vol. 22, pp. 503-529, 2004.
Larsen et al., "Suppressors of Cytokine Signalling: SOCS," APMIS, vol. 110, pp. 833-844, 2002.
Jun. 18, 2013 Supplementary European Search Report issued in European Application No. 10 82 6811.

(Continued)

*Primary Examiner* — Kimberly A Ballard
(74) *Attorney, Agent, or Firm* — Oliff PLC

(57) ABSTRACT

A neuronal differentiation inducer provided by the present invention contains an artificially synthesized peptide which includes an amino acid sequence constituting a signal peptide in amyloid precursor protein (APP), or a partial sequence of the amino acid sequence constituting this signal peptide.

14 Claims, 12 Drawing Sheets

(56) References Cited

OTHER PUBLICATIONS

Bochkov et al., "Phylogenetic Analysis of Partial S1 and N Gene Sequences of Infections Bronchitis Virus Isolates from Italy Revealed Genetic Diversity and Recombination," Virus Genes, vol. 35, pp. 65-71, 2007.
Boursnell et al., "Sequences of the Nucleocapsid Genes from Two Strains of Avian Infectious Bronchitis Virus," J. Gen. Virol., vol. 66, pp. 573-580, 1985.
Cserpán et al., "The Mechanism of Nuclear Transport of Natural or Artificial Transport Substrates in Digitonin-Permeabilized Cells," Journal of Cell Science, vol. 108, pp. 1849-1861, 1995.
Eiges et al., "Establishment of Human Embryonic Stem Cell-Transfected Clones Carrying a Marker for Undifferentiated Cells," Current Biology, vol. 11, pp. 514-518, 2001.
Emmott et al., "Nucleolar Targeting: The Hub of the Matter," European Molecular Biology Organization, vol. 10, No. 3, pp. 231-238, 2009.
Fang et al., "Selection of and Recombination between Minor Variants Lead to the Adaptation of an Avian Coronavirus to Primate Cells," Biochemical and Biophysical Research Communications, vol. 336, pp. 417-423, 2005.
Futaki et al., "Intracellular Protein Delivery Using Membrane-Permeable Peptides," Seibutsu to Kagaku, vol. 43, No. 10, pp. 649-653, 2005, with English-language translation.
Hilton et al., "Twenty Proteins Containg a C-Terminal SOCS Box Form Five Structural Classes," Proc. Natl. Acad. Sci. USA, vol. 95, pp. 114-119, Jan. 1998.
Kamura et al., "The Elongin BC Complex Interacts with the Conserved SOCS-Box Motif Present in Members of the SOCS, Ras, WD-40 Repeat, and Ankyrin Repeat Families," Genes & Development, vol. 12, pp. 3872-3881, 1998.
Kamura et al., "VHL-Box and SOCS-Box Domains Determine Binding Specificity for Cu12-Rbx1 and Cu15-Rbx2 Modules of Ubiquitin Ligases," Genes & Development, vol. 18, pp. 3055-3065, 2004.
Kile et al., "The Suppressors of Cytokine Signalling (SOCS)," Cellular and Molecular Life Sciences, vol. 58, pp. 1627-1635, 2001.
Kobayashi et al., "Nucleolar Localization Signals of LIM Kinase 2 Function as a Cell-Penetrating Peptide," Protein & Peptide Letters, vol. 17, pp. 1480-1488, 2010.
Liu et al., "Rack1 Competes with HSP90 for Binding to HIF-1α and is Required for $O_2$-Independent and HSP90 Inhibitor-Induced Degradation of HIF-α," Molecular Cell, vol. 25, pp. 207-217, Jan. 26, 2007.
Liu et al., "Calcineurin Promotes Hypoxia-Inducible Factor 1α Expression by Dephosphorylating RACK1 and Blocking Rack1 Dimerization," Journal of Biological Chemistry, vol. 282, No. 51, pp. 37064-37073, Dec. 21, 2007.
Liu et al., "Rack1 vs. HSP90: Competition for HIF-1α Degradation vs. Stablization," Cell Cycle, vol. 6, No. 6, pp. 656-659, Mar. 15, 2007.
NCBI database Accession No. Q1M2X0, p. 1, accessed Nov. 7, 2012.
Pokorska 20μm 20μm 20μm 20μm 20μm 20μm 20µm 20μm 20μm ├─┤
20μm ├─┤
20μm 20μm 20μm 20μm 20μm

SEQUENCE LISTING

```
<160> NUMBER OF SEQ ID NOS: 35

<210> SEQ ID NO 1
<211> LENGTH: 13
<212> TYPE: PRT
<213> ORGANISM: Artificial sequence
<220> FEATURE:
<223> OTHER INFORMATION: Synthetic peptide

<400> SEQUENCE: 1

Lys Lys Arg Thr Leu Arg Lys Asn Asp Arg Lys Lys Arg
1               5                   10

<210> SEQ ID NO 2
<211> LENGTH: 17
<212> TYPE: PRT
<213> ORGANISM: Artificial sequence
<220> FEATURE:
<223> OTHER INFORMATION: Synthetic peptide
```

```
<400> SEQUENCE: 2

Met Leu Pro Gly Leu Ala Leu Leu Leu Ala Ala Trp Thr Ala Arg
1               5                   10                  15

Ala

<210> SEQ ID NO 3
<211> LENGTH: 17
<212> TYPE: PRT
<213> ORGANISM: Artificial sequence
<220> FEATURE:
<223> OTHER INFORMATION: Synthetic peptide

<400> SEQUENCE: 3

Met Leu Pro Ser Leu Ala Leu Leu Leu Ala Ala Trp Thr Val Arg
1               5                   10                  15

Ala

<210> SEQ ID NO 4
<211> LENGTH: 31
<212> TYPE: PRT
<213> ORGANISM: Artificial sequence
<220> FEATURE:
<223> OTHER INFORMATION: Synthetic peptide

<400> SEQUENCE: 4

Met Leu Pro Gly Leu Ala Leu Leu Leu Ala Ala Trp Thr Ala Arg
1               5                   10                  15

Ala Gly Lys Lys Arg Thr Leu Arg Lys Asn Asp Arg Lys Lys Arg
            20                  25                  30

<210> SEQ ID NO 5
<211> LENGTH: 30
<212> TYPE: PRT
<213> ORGANISM: Artificial sequence
<220> FEATURE:
<223> OTHER INFORMATION: Synthetic peptide

<400> SEQUENCE: 5

Leu Pro Gly Leu Ala Leu Leu Leu Ala Ala Trp Thr Ala Arg Ala
1               5                   10                  15

Gly Lys Lys Arg Thr Leu Arg Lys Asn Asp Arg Lys Lys Arg
            20                  25                  30

<210> SEQ ID NO 6
<211> LENGTH: 29
<212> TYPE: PRT
<213> ORGANISM: Artificial sequence
<220> FEATURE:
<223> OTHER INFORMATION: Synthetic peptide

<400> SEQUENCE: 6

Pro Gly Leu Ala Leu Leu Leu Ala Ala Trp Thr Ala Arg Ala Gly
1               5                   10                  15

Lys Lys Arg Thr Leu Arg Lys Asn Asp Arg Lys Lys Arg
            20                  25

<210> SEQ ID NO 7
<211> LENGTH: 28
<212> TYPE: PRT
<213> ORGANISM: Artificial sequence
<220> FEATURE:
<223> OTHER INFORMATION: Synthetic peptide

<400> SEQUENCE: 7
```

Gly Leu Ala Leu Leu Leu Ala Ala Trp Thr Ala Arg Ala Gly Lys
1               5                   10                  15

Lys Arg Thr Leu Arg Lys Asn Asp Arg Lys Lys Arg
            20                  25

<210> SEQ ID NO 8
<211> LENGTH: 27
<212> TYPE: PRT
<213> ORGANISM: Artificial sequence
<220> FEATURE:
<223> OTHER INFORMATION: Synthetic peptide

<400> SEQUENCE: 8

Leu Ala Leu Leu Leu Ala Ala Trp Thr Ala Arg Ala Gly Lys Lys
1               5                   10                  15

Arg Thr Leu Arg Lys Asn Asp Arg Lys Lys Arg
            20                  25

<210> SEQ ID NO 9
<211> LENGTH: 26
<212> TYPE: PRT
<213> ORGANISM: Artificial sequence
<220> FEATURE:
<223> OTHER INFORMATION: Synthetic peptide

<400> SEQUENCE: 9

Ala Leu Leu Leu Ala Ala Trp Thr Ala Arg Ala Gly Lys Lys Arg
1               5                   10                  15

Thr Leu Arg Lys Asn Asp Arg Lys Lys Arg
            20                  25

<210> SEQ ID NO 10
<211> LENGTH: 25
<212> TYPE: PRT
<213> ORGANISM: Artificial sequence
<220> FEATURE:
<223> OTHER INFORMATION: Synthetic peptide

<400> SEQUENCE: 10

Leu Leu Leu Ala Ala Trp Thr Ala Arg Ala Gly Lys Lys Arg Thr
1               5                   10                  15

Leu Arg Lys Asn Asp Arg Lys Lys Arg
            20                  25

<210> SEQ ID NO 11
<211> LENGTH: 24
<212> TYPE: PRT
<213> ORGANISM: Artificial sequence
<220> FEATURE:
<223> OTHER INFORMATION: Synthetic peptide

<400> SEQUENCE: 11

Leu Leu Ala Ala Trp Thr Ala Arg Ala Gly Lys Lys Arg Thr Leu
1               5                   10                  15

Arg Lys Asn Asp Arg Lys Lys Arg
            20

<210> SEQ ID NO 12
<211> LENGTH: 23
<212> TYPE: PRT
<213> ORGANISM: Artificial sequence
<220> FEATURE:
<223> OTHER INFORMATION: Synthetic peptide

<400> SEQUENCE: 12

```
Leu Leu Ala Ala Trp Thr Ala Arg Ala Gly Lys Lys Arg Thr Leu Arg
1               5                   10                  15

Lys Asn Asp Arg Lys Lys Arg
            20
```

<210> SEQ ID NO 13
<211> LENGTH: 22
<212> TYPE: PRT
<213> ORGANISM: Artificial sequence
<220> FEATURE:
<223> OTHER INFORMATION: Synthetic peptide

<400> SEQUENCE: 13

```
Leu Ala Ala Trp Thr Ala Arg Ala Gly Lys Lys Arg Thr Leu Arg Lys
1               5                   10                  15

Asn Asp Arg Lys Lys Arg
            20
```

<210> SEQ ID NO 14
<211> LENGTH: 21
<212> TYPE: PRT
<213> ORGANISM: Artificial sequence
<220> FEATURE:
<223> OTHER INFORMATION: Synthetic peptide

<400> SEQUENCE: 14

```
Ala Ala Trp Thr Ala Arg Ala Gly Lys Lys Arg Thr Leu Arg Lys Asn
1               5                   10                  15

Asp Arg Lys Lys Arg
            20
```

<210> SEQ ID NO 15
<211> LENGTH: 20
<212> TYPE: PRT
<213> ORGANISM: Artificial sequence
<220> FEATURE:
<223> OTHER INFORMATION: Synthetic peptide

<400> SEQUENCE: 15

```
Ala Trp Thr Ala Arg Ala Gly Lys Lys Arg Thr Leu Arg Lys Asn Asp
1               5                   10                  15

Arg Lys Lys Arg
            20
```

<210> SEQ ID NO 16
<211> LENGTH: 19
<212> TYPE: PRT
<213> ORGANISM: Artificial sequence
<220> FEATURE:
<223> OTHER INFORMATION: Synthetic peptide

<400> SEQUENCE: 16

```
Trp Thr Ala Arg Ala Gly Lys Lys Arg Thr Leu Arg Lys Asn Asp Arg
1               5                   10                  15

Lys Lys Arg
```

<210> SEQ ID NO 17
<211> LENGTH: 31
<212> TYPE: PRT
<213> ORGANISM: Artificial sequence
<220> FEATURE:
<223> OTHER INFORMATION: Synthetic peptide

<400> SEQUENCE: 17

Met Leu Pro Ser Leu Ala Leu Leu Leu Ala Ala Trp Thr Val Arg
1               5                   10                  15

Ala Gly Lys Lys Arg Thr Leu Arg Lys Asn Asp Arg Lys Lys Arg
            20                  25                  30

<210> SEQ ID NO 18
<211> LENGTH: 30
<212> TYPE: PRT
<213> ORGANISM: Artificial sequence
<220> FEATURE:
<223> OTHER INFORMATION: Synthetic peptide

<400> SEQUENCE: 18

Leu Pro Ser Leu Ala Leu Leu Leu Ala Ala Trp Thr Val Arg Ala
1               5                   10                  15

Gly Lys Lys Arg Thr Leu Arg Lys Asn Asp Arg Lys Lys Arg
            20                  25                  30

<210> SEQ ID NO 19
<211> LENGTH: 29
<212> TYPE: PRT
<213> ORGANISM: Artificial sequence
<220> FEATURE:
<223> OTHER INFORMATION: Synthetic peptide

<400> SEQUENCE: 19

Pro Ser Leu Ala Leu Leu Leu Ala Ala Trp Thr Val Arg Ala Gly
1               5                   10                  15

Lys Lys Arg Thr Leu Arg Lys Asn Asp Arg Lys Lys Arg
            20                  25

<210> SEQ ID NO 20
<211> LENGTH: 28
<212> TYPE: PRT
<213> ORGANISM: Artificial sequence
<220> FEATURE:
<223> OTHER INFORMATION: Synthetic peptide

<400> SEQUENCE: 20

Ser Leu Ala Leu Leu Leu Ala Ala Trp Thr Val Arg Ala Gly Lys
1               5                   10                  15

Lys Arg Thr Leu Arg Lys Asn Asp Arg Lys Lys Arg
            20                  25

<210> SEQ ID NO 21
<211> LENGTH: 27
<212> TYPE: PRT
<213> ORGANISM: Artificial sequence
<220> FEATURE:
<223> OTHER INFORMATION: Synthetic peptide

<400> SEQUENCE: 21

Leu Ala Leu Leu Leu Ala Ala Trp Thr Val Arg Ala Gly Lys Lys
1               5                   10                  15

Arg Thr Leu Arg Lys Asn Asp Arg Lys Lys Arg
            20                  25

<210> SEQ ID NO 22
<211> LENGTH: 26
<212> TYPE: PRT
<213> ORGANISM: Artificial sequence
<220> FEATURE:
<223> OTHER INFORMATION: Synthetic peptide

<400> SEQUENCE: 22

Ala Leu Leu Leu Leu Ala Ala Trp Thr Val Arg Ala Gly Lys Lys Arg
1               5                   10                  15

Thr Leu Arg Lys Asn Asp Arg Lys Lys Arg
            20                  25

<210> SEQ ID NO 23
<211> LENGTH: 25
<212> TYPE: PRT
<213> ORGANISM: Artificial sequence
<220> FEATURE:
<223> OTHER INFORMATION: Synthetic peptide

<400> SEQUENCE: 23

Leu Leu Leu Leu Ala Ala Trp Thr Val Arg Ala Gly Lys Lys Arg Thr
1               5                   10                  15

Leu Arg Lys Asn Asp Arg Lys Lys Arg
            20                  25

<210> SEQ ID NO 24
<211> LENGTH: 24
<212> TYPE: PRT
<213> ORGANISM: Artificial sequence
<220> FEATURE:
<223> OTHER INFORMATION: Synthetic peptide

<400> SEQUENCE: 24

Leu Leu Leu Ala Ala Trp Thr Val Arg Ala Gly Lys Lys Arg Thr Leu
1               5                   10                  15

Arg Lys Asn Asp Arg Lys Lys Arg
            20

<210> SEQ ID NO 25
<211> LENGTH: 23
<212> TYPE: PRT
<213> ORGANISM: Artificial sequence
<220> FEATURE:
<223> OTHER INFORMATION: Synthetic peptide

<400> SEQUENCE: 25

Leu Leu Ala Ala Trp Thr Val Arg Ala Gly Lys Lys Arg Thr Leu Arg
1               5                   10                  15

Lys Asn Asp Arg Lys Lys Arg
            20

<210> SEQ ID NO 26
<211> LENGTH: 22
<212> TYPE: PRT
<213> ORGANISM: Artificial sequence
<220> FEATURE:
<223> OTHER INFORMATION: Synthetic peptide

<400> SEQUENCE: 26

Leu Ala Ala Trp Thr Val Arg Ala Gly Lys Lys Arg Thr Leu Arg Lys
1               5                   10                  15

Asn Asp Arg Lys Lys Arg
            20

<210> SEQ ID NO 27
<211> LENGTH: 21
<212> TYPE: PRT
<213> ORGANISM: Artificial sequence
<220> FEATURE:
<223> OTHER INFORMATION: Synthetic peptide

<400> SEQUENCE: 27

```
Ala Ala Trp Thr Val Arg Ala Gly Lys Lys Arg Thr Leu Arg Lys Asn
1               5                   10                  15

Asp Arg Lys Lys Arg
            20
```

<210> SEQ ID NO 28
<211> LENGTH: 20
<212> TYPE: PRT
<213> ORGANISM: Artificial sequence
<220> FEATURE:
<223> OTHER INFORMATION: Synthetic peptide

<400> SEQUENCE: 28

```
Ala Trp Thr Val Arg Ala Gly Lys Lys Arg Thr Leu Arg Lys Asn Asp
1               5                   10                  15

Arg Lys Lys Arg
            20
```

<210> SEQ ID NO 29
<211> LENGTH: 19
<212> TYPE: PRT
<213> ORGANISM: Artificial sequence
<220> FEATURE:
<223> OTHER INFORMATION: Synthetic peptide

<400> SEQUENCE: 29

```
Trp Thr Val Arg Ala Gly Lys Lys Arg Thr Leu Arg Lys Asn Asp Arg
1               5                   10                  15

Lys Lys Arg
```

<210> SEQ ID NO 30
<211> LENGTH: 20
<212> TYPE: PRT
<213> ORGANISM: Artificial sequence
<220> FEATURE:
<223> OTHER INFORMATION: Synthetic peptide

<400> SEQUENCE: 30

```
Met Leu Pro Gly Leu Ala Gly Lys Lys Arg Thr Leu Arg Lys Asn Asp
1               5                   10                  15

Arg Lys Lys Arg
            20
```

<210> SEQ ID NO 31
<211> LENGTH: 20
<212> TYPE: PRT
<213> ORGANISM: Artificial sequence
<220> FEATURE:
<223> OTHER INFORMATION: Synthetic peptide

<400> SEQUENCE: 31

```
Met Leu Pro Ser Leu Ala Gly Lys Lys Arg Thr Leu Arg Lys Asn Asp
1               5                   10                  15

Arg Lys Lys Arg
            20
```

<210> SEQ ID NO 32
<211> LENGTH: 20
<212> TYPE: PRT
<213> ORGANISM: Artificial sequence
<220> FEATURE:
<223> OTHER INFORMATION: Synthetic peptide

<400> SEQUENCE: 32

```
Leu Leu Leu Leu Ala Ala Gly Lys Lys Arg Thr Leu Arg Lys Asn Asp
```

```
1               5                  10                 15
Arg Lys Lys Arg
            20

<210> SEQ ID NO 33
<211> LENGTH: 11
<212> TYPE: PRT
<213> ORGANISM: Artificial sequence
<220> FEATURE:
<223> OTHER INFORMATION: Synthetic peptide

<400> SEQUENCE: 33

Tyr Gly Arg Lys Lys Arg Arg Gln Arg Arg
1               5                  10

<210> SEQ ID NO 34
<211> LENGTH: 11
<212> TYPE: PRT
<213> ORGANISM: Artificial sequence
<220> FEATURE:
<223> OTHER INFORMATION: Synthetic peptide

<400> SEQUENCE: 34

Tyr Ala Arg Ala Ala Ala Arg Gln Ala Arg Ala
1               5                  10

<210> SEQ ID NO 35
<211> LENGTH: 18
<212> TYPE: PRT
<213> ORGANISM: Artificial sequence
<220> FEATURE:
<223> OTHER INFORMATION: Synthetic peptide

<400> SEQUENCE: 35

Lys Gly Arg Gln Val Lys Val Trp Phe Gln Asn Arg Arg Met Lys Trp
1               5                  10                 15

Lys Lys
```

NEURONAL DIFFERENTIATION-INDUCING PEPTIDE AND USE THEREOF

TECHNICAL FIELD

The present invention relates to a neuronal differentiation-inducing peptide and the use thereof. More particularly, the invention relates to a neuronal differentiation inducer containing such a peptide as the active ingredient.

This application claims priority from Japanese Patent Application No. 2009-095641, filed on Apr. 10, 2009, the entire contents of which are incorporated herein by reference.

BACKGROUND ART

One challenge in the field of regenerative medicine is the regeneration of nerve cells. It is hoped, for example, that the regeneration of nerve cells using neuronal stem cells or embryonic stem cells (ES cells) will lead to treatments for central nervous system diseases such as Parkinson disease and Alzheimer disease (Patent Document 1). However, embryonic and other stem cells are difficult to acquire (collect). Moreover, even when such stem cells are implanted directly to the affected area, substantially no differentiation to nerve cells occurs and engraftment is difficult. Even in cases where such cells do take, few if any end up differentiating to glia cells.

Somatic (adult) stem cells such as neuronal stem cells, skin stem cells and adipose stem cells are stem cells that are relatively easy to acquire. Were it possible to differentiate such stem cells to nerve cells, their utility in the healthcare industry would be high. However, a method for inducing the differentiation of nerve cells from these somatic stem cells in a short period of time and at a high efficiency has yet to be established. Hence, there exists a desire for such a method to be established; that is, for the development of a neuronal differentiation inducer suitable for such a purpose. For example, Patent Document 2 discloses a neuronal differentiation inducer containing a pyrrolidone derivative as the active ingredient, but it does not disclose the effects of inducing the differentiation of nerve cells from somatic stem cells.

Recently, the use of peptides having the function of inducing the differentiation of stem cells to nerve cells (neuronal differentiation-inducing peptides) has been attracting attention. For example, Patent Document 3 describes a peptide (VHL peptide) which is capable of inducing neuronal differentiation from neuronal stem cells or skin stem cells.

Patent Document 1: Japanese Patent Application Laid-open No. 2004-357543
Patent Document 2: Japanese Patent Application Laid-open No. H9-323928
Patent Document 3: Japanese Patent Application Laid-open No. 2005-330206
Non-Patent Document 1: *Trends in Cell Biology*, 8, 410-415 (1998)
Non-Patent Document 2: *The Journal of Biological Chemistry*, 281(35), 25223-25230 (2006)

DISCLOSURE OF THE INVENTION

The present invention was conceived by taking an approach which differs from the approach taken in developing neuronal differentiation inducers containing conventional chemical substances such as that described in Patent Document 2. The object of this invention is to provide a synthetic peptide having a higher neuronal differentiation-inducing activity than known neuronal differentiation-inducing peptides like those mentioned in Patent Document 3. A further object is to provide neuronal differentiation inducers (pharmaceutical compositions) in which such peptides serve as the active ingredients. A still further object is to provide a method of producing nerve cells using such peptides, and a method of inducing the development of nerve cells.

The neuronal differentiation-inducing peptide provided by the invention is a synthetic peptide which has been artificially designed and does not exist alone by itself as a neuronal differentiation-inducing peptide in the natural world.

The inventors have closely investigated the amyloid precursor protein. In the amyloid hypothesis according to which amyloid precursor protein (APP) is cleaved by secretase, producing amyloid β protein (typically composed of 40 or 42 amino acid residues) which aggregates (builds up) within the brain, thereby destroying nerve cells and leading to the onset of Alzheimer disease, the amyloid precursor protein may be considered the starting substance for Alzheimer disease. In the course of their investigations, the inventors have paid particularly close attention to the signal peptide of this amyloid precursor protein.

In addition, the inventors have discovered that synthetic peptide created so as to include all or part of the amino acid sequence constituting the signal peptide in amyloid precursor protein has a high neuronal differentiation-inducing activity on various stem cells, which discovery ultimately led to the present invention.

The inventors have also discovered that the amino acid sequence known as the nucleolar localization signal (NoLS) (see Non-Patent Document 2) is an amino acid sequence which takes part in extracellular to intranuclear (typically, the nucleolus) peptide migration, and that by using a synthetic peptide constituted so as to include this amino acid sequence, the efficiency of differentiation from stem cells to nerve cells can be greatly increased.

The neuronal differentiation-inducing peptide disclosed herein is a peptide which is capable of inducing the differentiation of at least one type of stem cell to a nerve cell (Hereinafter, the term "neuronal differentiation-inducing peptide" means this peptide). In one embodiment, the neuronal differentiation-inducing peptide of the present invention includes an amino acid sequence constituting a signal peptide in amyloid precursor protein (APP).

In another embodiment, the neuronal differentiation-inducing peptide of the invention includes an N-terminal side partial amino acid sequence which is part of the amino acid sequence constituting the above signal peptide and is composed of at least six consecutive amino acid residues counting from the N-terminal amino acid residue of this sequence.

In yet another embodiment, the neuronal differentiation-inducing peptide of the invention includes a C-terminal side partial amino acid sequence which is part of the amino acid sequence constituting the above signal peptide and is composed of at least five consecutive amino acid residues counting from the C-terminal amino acid residue of this sequence.

In the present specification, the amino acid sequence constituting a signal peptide in amyloid precursor protein (APP) and the partial amino acid sequence in such a signal peptide sequence (that is, the N-terminal side partial amino acid sequence or C-terminal side partial amino acid sequence) which is included in the neuronal differentiation-inducing peptide disclosed herein are collectively referred to as the "APP signal peptide-related sequence."

Also, in the amino acid sequences appearing in this specification, the left side is always the N-terminal side and the right side is always the C-terminal side.

In a preferred embodiment of the neuronal differentiation-inducing peptide disclosed herein, the amyloid precursor protein signal peptide is the amino acid sequence MLPGLALLLLAAWTARA (SEQ ID NO: 2) or MLPSLALLLLAAWTVRA (SEQ ID NO: 3), and the APP signal peptide-related sequence is the amino acid sequence of SEQ ID NO: 2 or SEQ ID NO: 3, or an N-terminal side partial amino acid sequence which is part of the amino acid sequence of SEQ ID NO: 2 or SEQ ID NO: 3 and is composed of at least six consecutive amino acid residues counting from the N-terminal amino acid residue of the sequence, or a C-terminal side partial amino acid sequence which is part of the amino acid sequence of SEQ ID NO: 2 or SEQ ID NO: 3 and is composed of at least five consecutive amino acid residues counting from the C-terminal amino acid residue of the sequence. These APP signal peptide related sequences may include, aside from the respective amino acid sequences of SEQ ID NO: 2 and SEQ ID NO: 3, modified amino acid sequences obtained by the partial modification of these amino acid sequences.

In another preferred embodiment of the neuronal differentiation-inducing peptide disclosed herein, the peptide is an artificially synthesized peptide which further includes the following amino acid sequence constituting a nucleolar localization signal:

(SEQ ID NO: 1)
KKRTLRKNDRKKR.

In yet another preferred embodiment of the neuronal differentiation-inducing peptide disclosed herein, the peptide includes the APP signal peptide-related sequence on the N-terminal side of the amino acid sequence constituting the nucleolar localization signal.

In an especially preferred embodiment of the neuronal differentiation-inducing peptide disclosed herein, the total number of amino acid residues constituting the peptide is 50 or less.

Preferred examples of neuronal differentiation-inducing peptides provided by the invention include synthetic peptides composed of the amino acid sequence indicated in any one of the sequence numbers selected from among SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30 and SEQ ID NO: 31.

In another aspect, the invention provides a neuronal differentiation inducer which is capable of inducing the differentiation of at least one type of stem cell into a nerve cell, and which includes any one of the neuronal differentiation-inducing peptides disclosed herein and at least one pharmaceutically acceptable carrier.

That is, the neuronal differentiation inducer disclosed herein includes as a neuronal differentiation-inducing peptide an artificially synthesized peptide containing an amino acid sequence constituting a signal peptide in amyloid precursor protein (APP) or containing, as an APP signal peptide-related sequence, an N-terminal side partial amino acid sequence which is part of the amino acid sequence constituting the signal peptide and is composed of at least six consecutive amino acid residues counting from the N-terminal amino acid residue of the sequence or a C-terminal side partial amino acid sequence which is part of the amino acid sequence constituting the signal peptide and is composed of at least five consecutive amino acid residues counting from the C-terminal amino acid residue of the sequence.

Preferably, the signal peptide of the amyloid precursor protein has the following amino acid sequence: MLPGLALLLLAAWTARA (SEQ ID NO: 2) or MLPSLALLLLAAWTVRA (SEQ ID NO: 3), and the APP signal peptide-related sequence is the amino acid sequence of SEQ ID NO: 2 or SEQ ID NO: 3, or an N-terminal side partial amino acid sequence which is part of the amino acid sequence of SEQ ID NO: 2 or SEQ ID NO: 3 and is composed of at least six consecutive amino acid residues counting from the N-terminal amino acid residue of the sequence, or a C-terminal side partial amino acid sequence which is part of the amino acid sequence of SEQ ID NO: 2 or SEQ ID NO: 3 and is composed of at least five consecutive amino acid residues counting from the C-terminal amino acid residue of the sequence.

Also, the neuronal differentiation-inducing peptide included in the neuronal differentiation inducer is preferably an artificially synthesized peptide which additionally includes the following amino acid sequence constituting a nucleolar localization signal:

(SEQ ID NO: 1)
KKRTLRKNDRKKR.

It is also preferable for the neuronal differentiation-inducing peptide included in the neuronal differentiation inducer to include the APP signal peptide-related sequence on the N-terminal side of the amino acid sequence constituting the nucleolar localization signal, and especially preferable for the total number of amino acid residues constituting the peptide to be 50 or less.

Preferred examples of the neuronal differentiation-inducing peptide included in the neuronal differentiation inducer include synthetic peptides composed of the amino acid sequence indicated in any one of the sequence numbers selected from among SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30 and SEQ ID NO: 31.

In yet another aspect, the invention provides various methods which employ the neuronal differentiation inducer or neuronal differentiation-inducing peptide disclosed herein.

That is, the invention provides a method of producing nerve cells from at least one type of cell material. This method is characterized by preparing any one of the synthetic peptides disclosed herein or a neuronal differentiation inducer (pharmaceutical composition) containing the synthetic peptide, and supplying the peptide or neuronal differentiation inducer to the cell material.

The invention also provides a method of generating nerve cells in a living organism or in living tissue. This method is characterized by preparing any of the synthetic peptides disclosed herein or a neuronal differentiation inducer (pharmaceutical composition) containing the synthetic peptide, and supplying the synthetic peptide or the neuronal differentiation inducer (pharmaceutical composition) containing the synthetic peptide to a living organism or to living tissue which has been temporarily or permanently removed from a living organism.

The invention additionally provides an artificially designed polynucleotide which does not exist in nature and which includes a nucleotide sequence encoding any one of the synthetic peptides disclosed herein and/or a nucleotide sequence complementary to such a sequence (e.g., polynucleotides substantially composed of these sequences).

Examples of preferred polynucleotides include polynucleotides containing a nucleotide sequence encoding an amino acid sequence shown in any one of SEQ ID NOS: 4 to 31 and/or a nucleotide sequence complementary to such a sequence (e.g., polynucleotides substantially composed of these sequences).

Because the neuronal differentiation-inducing peptide of the invention is, as mentioned above, a synthetic peptide having a simple construction which includes an APP signal peptide-related sequence (preferably an amino acid sequence composed of an APP signal peptide-related sequence and a nucleolar localization signal (NoLS)), it can easily be produced. Hence, the desired amount of peptide (and, by extension, the neuronal differentiating inducer) can easily be prepared.

Moreover, according to this invention, by utilizing such a neuronal differentiation-inducing peptide (neuronal differentiation inducer), inducing the differentiation of non-neuronal cells (typically somatic stem cells such as neuronal stem cells, adipose stem cells and skin stem cells, or embryonic stem cells) into nerve cells (neurons), which has hitherto been difficult, is easily achieved. Hence, by using cell materials which can be procured in relatively large quantities (adipose stem cells, etc.), it becomes possible to supply nerve cells in a desired amount according to the intended use (e.g., the treatment of neurological diseases requiring nerve regeneration). Alternatively, by administering a suitable amount to an affected area requiring nerve regeneration or to living tissue (including a culture such as a cell mass) which has been temporarily or permanently removed from a living organism, nerve cell generation can be achieved.

BEST MODE FOR CARRYING OUT THE INVENTION

Figure 1:
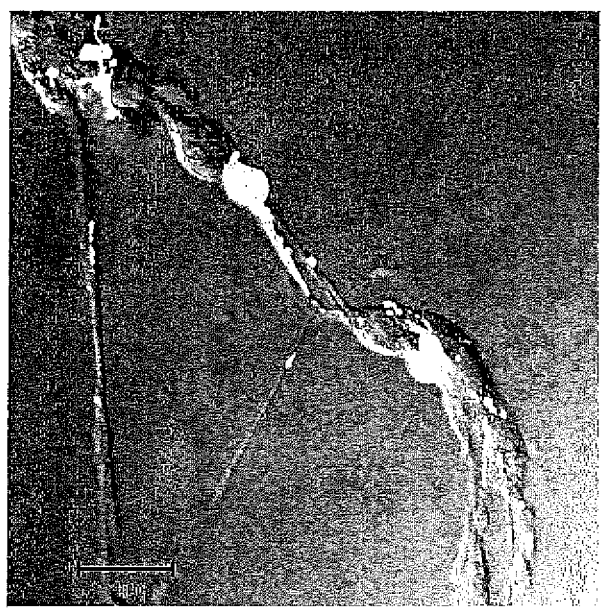
FIG. 1 is a fluorescence micrograph (image) obtained by adding a sample peptide (Sample 1) to a culture solution of mouse neuronal stem cells to a concentration within the solution of 0.5 µM and culturing for 7 days, then examining the state of neuronal differentiation by the cultured cells; the image was prepared by merging a differential interference contrast (DIC) image, a DAPI nuclear stain image, and a fluorescence image showing the results of an investigation by an immune antibody method using fluorochrome-labeled anti-tubulin antibody.
Figure 2:
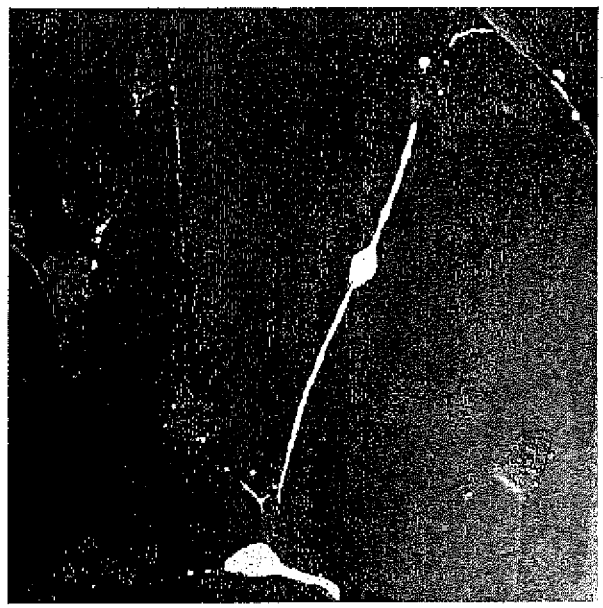
FIG. 2 is a fluorescence micrograph (image) obtained by examining the state of neuronal differentiation by cells which, aside from using Sample 2 as the peptide, were cultured under the same conditions and materials as when the fluorescence micrograph (image) of FIG. 1 was taken.
Figure 3:
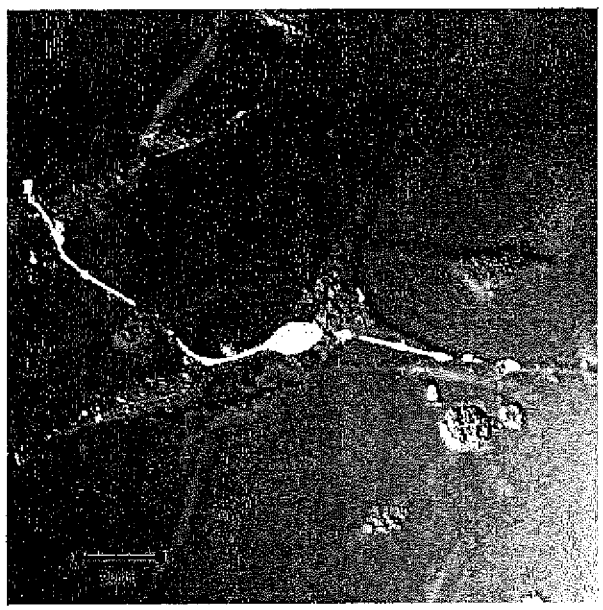
FIG. 3 is a fluorescence micrograph (image) obtained by examining the state of neuronal differentiation by cells which, aside from using Sample 3 as the peptide, were cultured under the same conditions and materials as when the fluorescence micrograph (image) of FIG. 1 was taken.
Figure 4:
FIG. 4 is a fluorescence micrograph (image) obtained by examining the state of neuronal differentiation by cells which, aside from using Sample 4 as the peptide, were cultured under the same conditions and materials as when the fluorescence micrograph (image) of FIG. 1 was taken.
Figure 5:
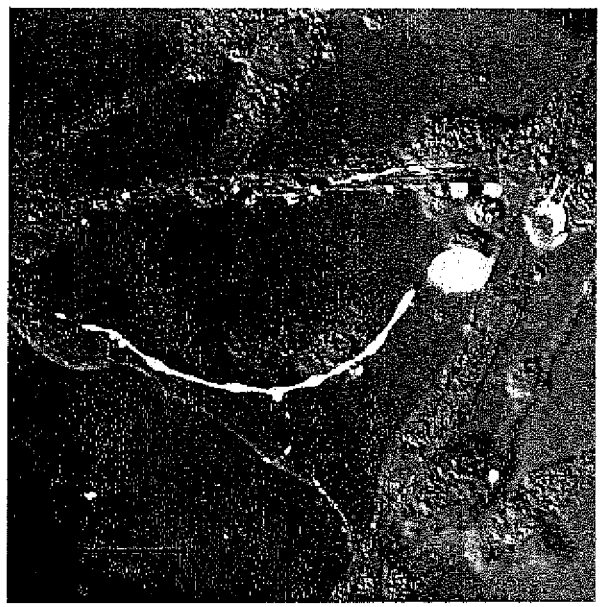
FIG. 5 is a fluorescence micrograph (image) obtained by examining the state of neuronal differentiation by cells which, aside from using Sample 5 as the peptide, were cultured under the same conditions and materials as when the fluorescence micrograph (image) of FIG. 1 was taken.
Figure 6:
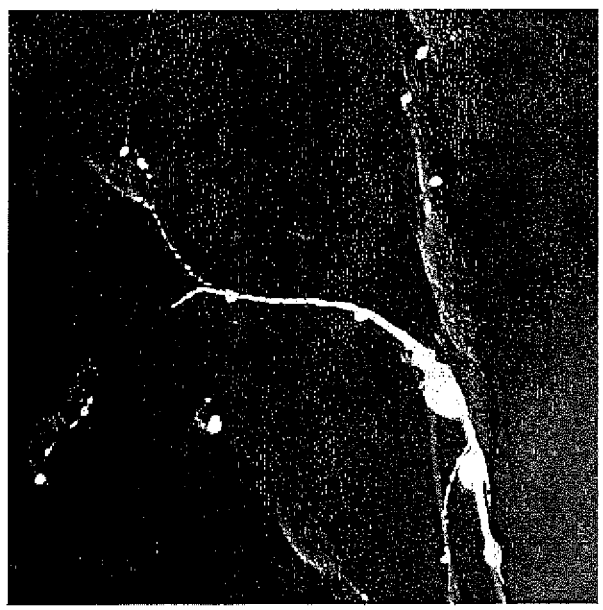
FIG. 6 is a fluorescence micrograph (image) obtained by examining the state of neuronal differentiation by cells which, aside from using Sample 6 as the peptide, were cultured under the same conditions and materials as when the fluorescence micrograph (image) of FIG. 1 was taken.
Figure 7:
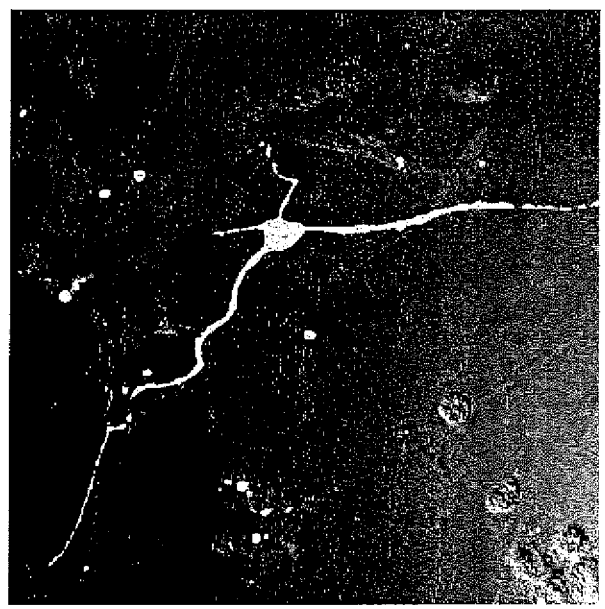
FIG. 7 is a fluorescence micrograph (image) obtained by examining the state of neuronal differentiation by cells which, aside from using Sample 7 as the peptide, were cultured under the same conditions and materials as when the fluorescence micrograph (image) of FIG. 1 was taken.
Figure 8:
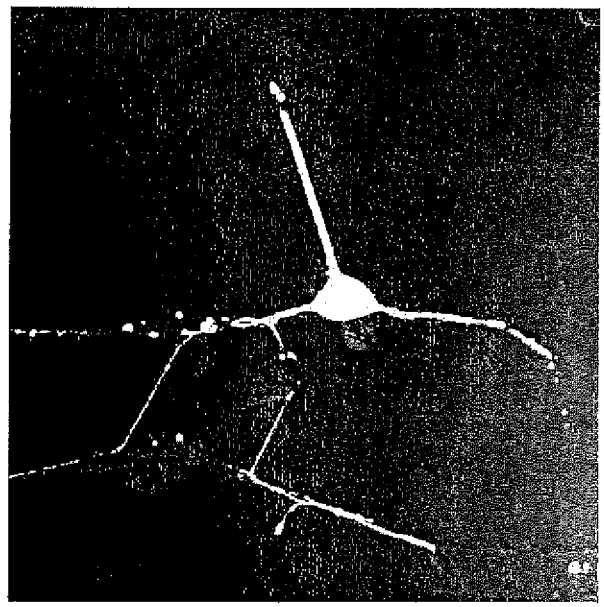
FIG. 8 is a fluorescence micrograph (image) obtained by examining the state of neuronal differentiation by cells which, aside from using Sample 8 as the peptide, were cultured under the same conditions and materials as when the fluorescence micrograph (image) of FIG. 1 was taken.
Figure 9:
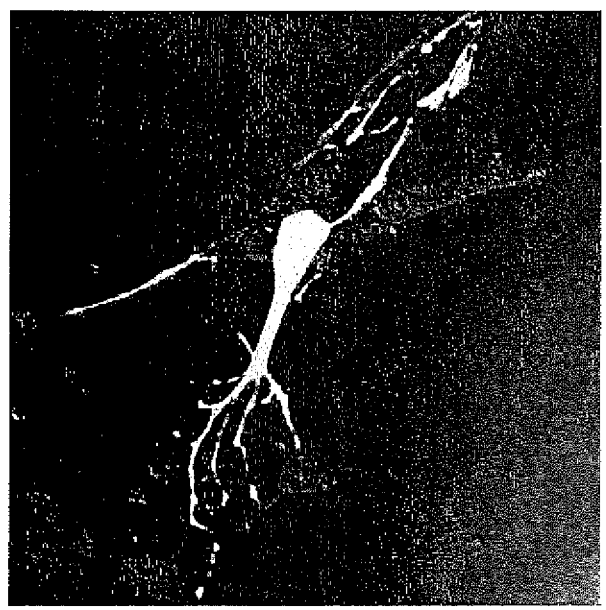
FIG. 9 is a fluorescence micrograph (image) obtained by examining the state of neuronal differentiation by cells which, aside from using Sample 9 as the peptide, were cultured under the same conditions and materials as when the fluorescence micrograph (image) of FIG. 1 was taken.
Figure 10:
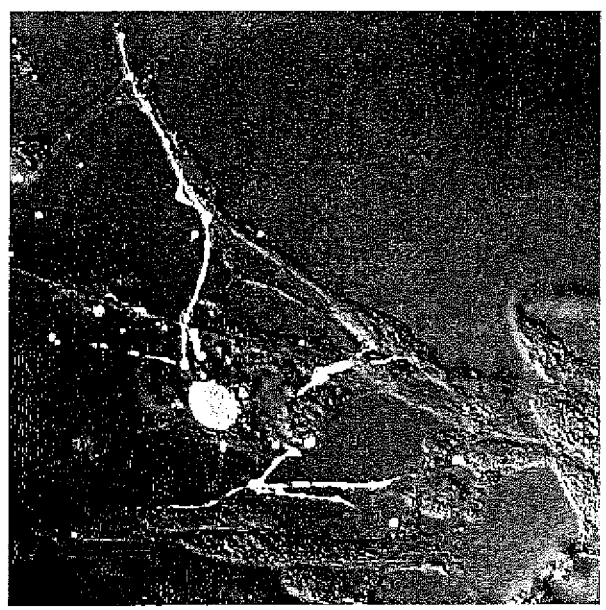
FIG. 10 is a fluorescence micrograph (image) obtained by examining the state of neuronal differentiation by cells which, aside from using Sample 10 as the peptide, were cultured under the same conditions and materials as when the fluorescence micrograph (image) of FIG. 1 was taken.
Figure 11:
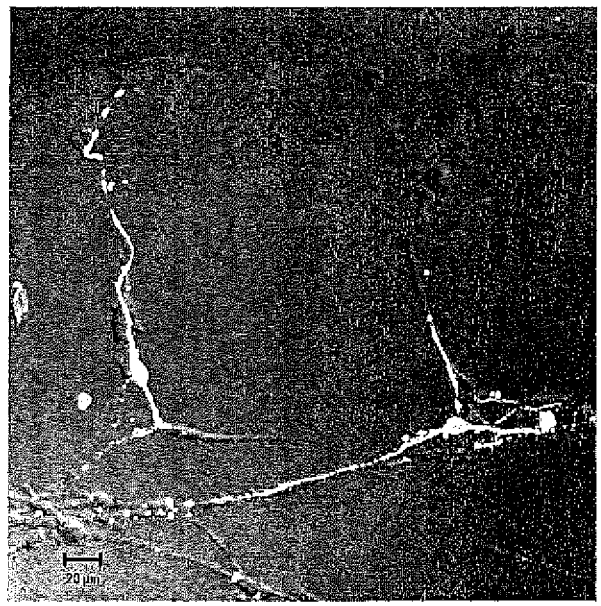
FIG. 11 is a fluorescence micrograph (image) obtained by examining the state of neuronal differentiation by cells which, aside from using Sample 11 as the peptide, were cultured under the same conditions and materials as when the fluorescence micrograph (image) of FIG. 1 was taken.
Figure 12:
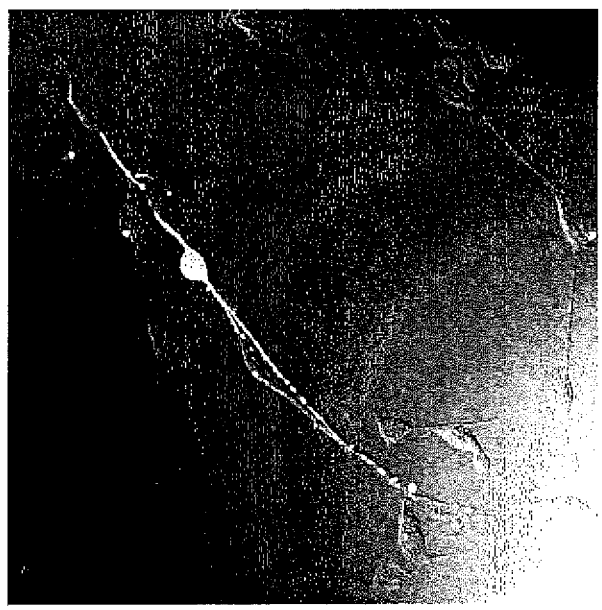
FIG. 12 is a fluorescence micrograph (image) obtained by examining the state of neuronal differentiation by cells which, aside from using Sample 12 as the peptide, were cultured under the same conditions and materials as when the fluorescence micrograph (image) of FIG. 1 was taken.
Figure 13:
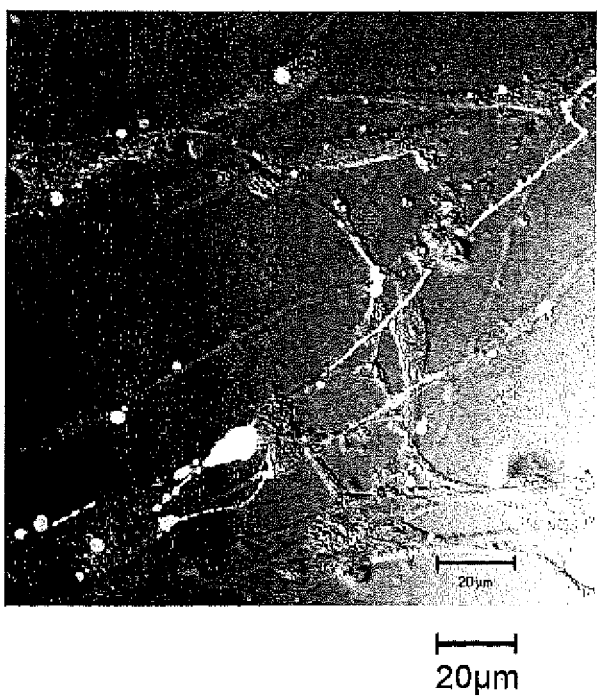
FIG. 13 is a fluorescence micrograph (image) obtained by examining the state of neuronal differentiation by cells which, aside from using Sample 13 as the peptide, were cultured under the same conditions and materials as when the fluorescence micrograph (image) of FIG. 1 was taken.
Figure 14:
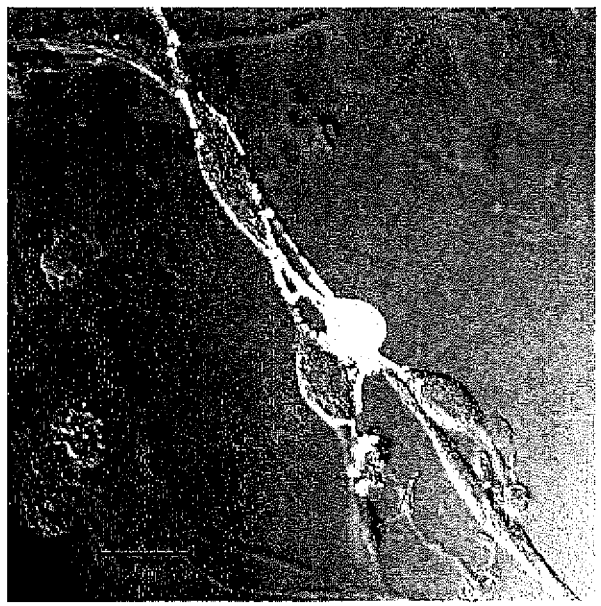
FIG. 14 is a fluorescence micrograph (image) obtained by examining the state of neuronal differentiation by cells which, aside from using Sample 14 as the peptide, were cultured under the same conditions and materials as when the fluorescence micrograph (image) of FIG. 1 was taken.
Figure 15:
FIG. 15 is a fluorescence micrograph (image) obtained by examining the state of neuronal differentiation by cells which, aside from using Sample 15 as the peptide, were cultured under the same conditions and materials as when the fluorescence micrograph (image) of FIG. 1 was taken.

Following is a detailed description of preferred embodiments of the invention. It will be appreciated that matters other than those specifically mentioned in the specification (such as the primary structure and chain length of neuronal differentiation-inducing peptides) which are nonetheless necessary for working the invention (e.g., general matters concerning peptide synthesis, polynucleotide synthesis and the preparation of neuronal differentiation inducers (pharmaceutical compositions) containing peptides as ingredients) are matters of design variation by persons of ordinary skill in the art based on prior art in the fields of medicine, pharmacology, organic chemistry, biochemistry, genetic engineering, protein engineering, molecular biology and public health. The present invention can be practiced based on details disclosed in the specification and common general technical knowledge in the field. In the following description, amino acids are indicated by single-letter designations (three-letter designations in the sequence listing) according to the nomenclature for amino acids set forth in the IUPAC-IUB guidelines.

The entire contents of all documents cited in this specification are incorporated herein by reference.

In the present specification, "artificially synthesized neuronal differentiation-inducing peptide" is not a peptide chain which by itself independently exists stably in the natural world, but refers to a peptide fragment manufactured by artificial chemical synthesis or biosynthesis (i.e., genetic engineering-based production) and is capable of existing stably within a predetermined system (e.g., a composition making up a neuronal differentiation inducer).

In this specification, "peptide" is a term which denotes an amino acid polymer having a plurality of peptide bonds. Although a peptide is not limited by the number of amino acid residues included on the peptide chain, the total number of amino acid residues is typically 100 or less, and preferably 50 or less.

As used herein, unless specified otherwise, "amino acid residue" is a term which includes the N-terminal amino acid and the C-terminal amino acid of a peptide chain. Also, in the specification, the phrase "an amino acid sequence that has been partially modified (modified amino acid sequence)," as used with respect to a particular amino acid sequence, refers to an amino acid sequence which was formed by substituting, deleting and/or adding (inserting) one or a plurality of (e.g., two or three) amino acid residues without a loss in the neuronal differentiation-inducing ability of the particular amino acid sequence. For example, sequences that arise due to conservative amino acid replacement by one or a plurality of (typically two or three) amino acid residues (e.g., a sequence in which a basic amino acid residue has been replaced with another basic amino acid residue), and sequences that arise when one or a plurality of (typically two or three) amino acid residues have been added (inserted) to or deleted from a particular amino acid sequence are typical examples encompassed by "an amino acid sequence that has been partially modified (modified amino acid sequence)" in this specification.

Also, in the specification, "polynucleotide" is a term denoting a polymer (nucleic acid) in which a plurality of nucleotides are linked by phosphodiester bonds, and is not limited by the number of nucleotides. As used herein, the term 'polynucleotide' encompasses DNA fragments and RNA fragments of various lengths. Also, "artificially designed polynucleotide" refers to a polynucleotide having a nucleotide chain (full length) which does not independently exist in the natural world but has been artificially synthesized, either by chemical synthesis or biosynthesis (i.e., genetic engineering-based production).

The inventors have discovered that relatively short peptides synthesized so as to include an amino acid sequence corresponding to the signal peptide of the amyloid precursor protein (APP) produced in the nerve cells of the brains of mammals such as humans, chimpanzees, crab-eating macaques, mice and rats are able to exhibit a remarkable neuronal differentiation-inducing activity. Although advances have been made lately in research on the function of signal peptides (for example, Non-Patent Document 1 is cited above as a review article), nowhere in the literature has it been suggested that the neuronal differentiation of at least one type of stem cell (e.g., various somatic stem cells, embryonic stem cells, synthetic pluripotent stem cells) is induced by the use of such APP signal peptide sequences.

The amino acid sequences of the amyloid precursor protein signal peptides preferably used in practicing the invention are shown respective in SEQ ID NO: 2 and SEQ ID NO: 3.

That is, the following amino acid sequence indicated as SEQ ID NO: 2

(SEQ ID NO: 2)
MLPGLALLLLAAWTARA is a signal peptide sequence composed of 17 amino acid residues in the amyloid precursor protein produced in the nerve cells of the brains of humans, chimpanzees and crab-eating macaques.

The following amino acid sequence indicated as SEQ ID NO: 3

(SEQ ID NO: 3)
MLPSLALLLLAAWTVRA is a signal peptide sequence composed of 17 amino acid residues in the amyloid precursor protein produced in the nerve cells of the brains of mice and rats.

When building the neuronal differentiation-inducing peptide of this invention, the amino acid sequence (composed of 17 amino acid residues) indicated in above SEQ ID NO: 2 or SEQ ID NO: 3 may be employed directly as the APP signal peptide-related sequence.

The N-terminal side partial amino acid sequence composed of at least six consecutive amino acid residues counting from the N-terminal amino acid residue on the signal peptide sequence of SEQ ID NO: 2 or SEQ ID NO: 3, that is, the N-terminal side partial amino acid sequence wherein the position 1 methionine residue to the position 6 alanine residue counting from the N-terminal amino acid residue are essential and amino acid residues to the C-terminal side therefrom are optional, can be used as the APP signal peptide-related sequence. Specific examples of the N-terminal side partial amino acid sequence include the following.

1. N-Terminal Side Partial Amino Acid Sequences from the Signal Peptide Sequence of SEQ ID NO: 2
(1) Sequences composed of a total of 6 amino acid residues from the position 1 methionine residue to the position 6 alanine residue, counting from the N-terminal amino acid residue;
(2) Sequences composed of a total of 7 amino acid residues from the position 1 methionine residue to the position 7 leucine residue, counting from the N-terminal amino acid residue;
(3) Sequences composed of a total of 8 amino acid residues from the position 1 methionine residue to the position 8 leucine residue, counting from the N-terminal amino acid residue;
(4) Sequences composed of a total of 9 amino acid residues from the position 1 methionine residue to the position 9 leucine residue, counting from the N-terminal amino acid residue;
(5) Sequences composed of a total of 10 amino acid residues from the position 1 methionine residue to the position 10 leucine residue, counting from the N-terminal amino acid residue;
(6) Sequences composed of a total of 11 amino acid residues from the position 1 methionine residue to the position 11 alanine residue, counting from the N-terminal amino acid residue;
(7) Sequences composed of a total of 12 amino acid residues from the position 1 methionine residue to the position 12 alanine residue, counting from the N-terminal amino acid residue;
(8) Sequences composed of a total of 13 amino acid residues from the position 1 methionine residue to the position 13 tryptophan residue, counting from the N-terminal amino acid residue;
(9) Sequences composed of a total of 14 amino acid residues from the position 1 methionine residue to the position 14 threonine residue, counting from the N-terminal amino acid residue;
(10) Sequences composed of a total of 15 amino acid residues from the position 1 methionine residue to the position 15 alanine residue, counting from the N-terminal amino acid residue; and
(11) Sequences composed of a total of 16 amino acid residues from the position 1 methionine residue to the position 16 arginine residue, counting from the N-terminal amino acid residue.

2. N-Terminal Side Partial Amino Acid Sequences from the Signal Peptide Sequence of SEQ ID NO: 3
(1) Sequences composed of a total of 6 amino acid residues from the position 1 methionine residue to the position 6 alanine residue, counting from the N-terminal amino acid residue;
(2) Sequences composed of a total of 7 amino acid residues from the position 1 methionine residue to the position 7 leucine residue, counting from the N-terminal amino acid residue;
(3) Sequences composed of a total of 8 amino acid residues from the position 1 methionine residue to the position 8 leucine residue, counting from the N-terminal amino acid residue;
(4) Sequences composed of a total of 9 amino acid residues from the position 1 methionine residue to the position 9 leucine residue, counting from the N-terminal amino acid residue;
(5) Sequences composed of a total of 10 amino acid residues from the position 1 methionine residue to the position 10 leucine residue, counting from the N-terminal amino acid residue;
(6) Sequences composed of a total of 11 amino acid residues from the position 1 methionine residue to the position 11 alanine residue, counting from the N-terminal amino acid residue;
(7) Sequences composed of a total of 12 amino acid residues from the position 1 methionine residue to the position 12 alanine residue, counting from the N-terminal amino acid residue;
(8) Sequences composed of a total of 13 amino acid residues from the position 1 methionine residue to the position 13 tryptophan residue, counting from the N-terminal amino acid residue;
(9) Sequences composed of a total of 14 amino acid residues from the position 1 methionine residue to the position 14 threonine residue, counting from the N-terminal amino acid residue;
(10) Sequences composed of a total of 15 amino acid residues from position 1 methionine residue to the position 15 valine residue, counting from the N-terminal amino acid residue; and
(11) Sequences composed of a total of 16 amino acid residues from the position 1 methionine residue to the position 16 arginine residue, counting from the N-terminal amino acid residue.

Alternatively, a C-terminal side partial amino acid sequence composed of at least five consecutive amino acid residues counting from the C-terminal amino acid residue of the signal peptide sequence of SEQ ID NO: 2 or SEQ ID NO: 3, that is, the C-terminal side partial amino acid sequence wherein the position 13 tryptophan residue to the position 17 (C-terminal) alanine residue counting from the N-terminal amino acid residue are essential and amino acid residues to the N-terminal side therefrom are optional, can be used as the APP signal peptide-related sequence. Specific examples of the C-terminal side partial amino acid sequence include the following.

3. C-Terminal Side Partial Amino Acid Sequences from the Signal Peptide Sequence of SEQ ID NO: 2
(1) Sequences composed of a total of 5 amino acid residues from the position 13 tryptophan residue to the position 17 (C-terminal) alanine residue, counting from the N-terminal amino acid residue;
(2) Sequences composed of a total of 6 amino acid residues from the position 12 alanine residue to the position 17 (C-terminal) alanine residue, counting from the N-terminal amino acid residue;
(3) Sequences composed of a total of 7 amino acid residues from the position 11 alanine residue to the position 17 (C-terminal) alanine residue, counting from the N-terminal amino acid residue;
(4) Sequences composed of a total of 8 amino acid residues from the position 10 leucine residue to the position 17 (C-terminal) alanine residue, counting from the N-terminal amino acid residue;
(5) Sequences composed of a total of 9 amino acid residues from the position 9 leucine residue to the position 17 (C-terminal) alanine residue, counting from the N-terminal amino acid residue;
(6) Sequences composed of a total of 10 amino acid residues from the position 8 leucine residue to the position 17 (C-terminal) alanine residue, counting from the N-terminal amino acid residue;

(7) Sequences composed of a total of 11 amino acid residues from the position 7 leucine residue to the position 17 (C-terminal) alanine residue, counting from the N-terminal amino acid residue;
(8) Sequences composed of a total of 12 amino acid residues from the position 6 alanine residue to the position 17 (C-terminal) alanine residue, counting from the N-terminal amino acid residue;
(9) Sequences composed of a total of 13 amino acid residues from the position 5 leucine residue to the position 17 (C-terminal) alanine residue, counting from the N-terminal amino acid residue;
(10) Sequences composed of a total of 14 amino acid residues from the position 4 glycine residue to the position 17 (C-terminal) alanine residue, counting from the N-terminal amino acid residue;
(11) Sequences composed of a total of 15 amino acid residues from the position 3 proline residue to the position 17 (C-terminal) alanine residue, counting from the N-terminal amino acid residue; and
(12) Sequences composed of a total of 16 amino acid residues from the position 2 leucine residue to the position 17 (C-terminal) alanine residue, counting from the N-terminal amino acid residue.

4. C-Terminal Side Partial Amino Acid Sequences from the Signal Peptide Sequence of SEQ ID NO: 3

(1) Sequences composed of a total of 5 amino acid residues from the position 13 tryptophan residue to the position 17 (C-terminal) alanine residue, counting from the N-terminal amino acid residue;
(2) Sequences composed of a total of 6 amino acid residues from the position 12 alanine residue to the position 17 (C-terminal) alanine residue, counting from the N-terminal amino acid residue;
(3) Sequences composed of a total of 7 amino acid residues from the position 11 alanine residue to the position 17 (C-terminal) alanine residue, counting from the N-terminal amino acid residue;
(4) Sequences composed of a total of 8 amino acid residues from the position 10 leucine residue to the position 17 (C-terminal) alanine residue, counting from the N-terminal amino acid residue;
(5) Sequences composed of a total of 9 amino acid residues from the position 9 leucine residue to the position 17 (C-terminal) alanine residue, counting from the N-terminal amino acid residue;
(6) Sequences composed of a total of 10 amino acid residues from the position 8 leucine residue to the position 17 (C-terminal) alanine residue, counting from the N-terminal amino acid residue;
(7) Sequences composed of a total of 11 amino acid residues from the position 7 leucine residue to the position 17 (C-terminal) alanine residue, counting from the N-terminal amino acid residue;
(8) Sequences composed of a total of 12 amino acid residues from the position 6 alanine residue to the position 17 (C-terminal) alanine residue, counting from the N-terminal amino acid residue;
(9) Sequences composed of a total of 13 amino acid residues from the position 5 leucine residue to the position 17 (C-terminal) alanine residue, counting from the N-terminal amino acid residue;
(10) Sequences composed of a total of 14 amino acid residues from the position 4 serine residue to the position 17 (C-terminal) alanine residue, counting from the N-terminal amino acid residue;
(11) Sequences composed of a total of 15 amino acid residues from the position 3 proline residue to the position 17 (C-terminal) alanine residue, counting from the N-terminal amino acid residue; and
(12) Sequences composed of a total of 16 amino acid residues from the position 2 leucine residue to the position 17 (C-terminal) alanine residue, counting from the N-terminal amino acid residue.

The designed neuronal differentiation-inducing peptide may be a peptide composed solely of the above APP signal peptide-related sequence or a modified amino acid sequence thereof However, from the standpoint of enhancing the neuronal differentiation-inducing activity, the use of an amino acid sequence which constitutes a protein transduction domain is preferred. Preferred examples are shown in SEQ ID NOS: 33, 34 and 35. SEQ ID NO: 33 shows the amino acid sequence of the protein transduction domain included in the TAT of HIV, and a peptide composed of this sequence. SEQ ID NO: 34 shows the amino acid sequence of a protein transduction domain (PTD4) obtained by modifying the above TAT, and a peptide composed of this sequence. SEQ ID NO: 35 shows the ANT-related amino acid sequence of the fruit fly (Drosophila) variant Antennapedia. These protein transduction domains shown in the sequence listing are illustrative examples only, there being no intention here to limit the domains that can be used to those mentioned above. The various protein transduction domains which may be used to practice the invention are mentioned in numerous documents that were already published at the time this application was filed. The amino acid sequences of such protein transduction domains are easily knowable by ordinary search means.

The use of the following amino acid sequence

```
                                            (SEQ ID NO: 1)
              KKRTLRKNDRKKR
``` is especially preferred.

The inventors, as described in Non-Patent Document 2, have discovered that when a peptide containing an amino acid sequence composed of the amino acid sequence shown in above SEQ ID NO: 1, known as a nucleolar localization signal (NoLS), and other target amino acid sequences (relatively short sequences which can be related to some other function; i.e., peptide motifs) is synthesized and added to eukaryotic cells being cultured, the peptide is able to pass through the cell membrane of the target cells at a high efficiency, and also is able to pass through the nuclear membrane at a high efficiency.

Accordingly, the present invention, by constructing (synthesizing) an artificial peptide obtained by combining a target APP signal peptide-related sequence (peptide motif related to neuronal differentiation induction) and the amino acid sequence shown in SEQ ID NO: 1 above (also referred to below as "nucleolar localization signal-related sequence") and adding the artificial peptide to a target eukaryotic cell, enables the artificial peptide to be efficiently transferred from the eukaryotic cell exterior (outside the cell membrane) into the nucleus (preferably the nucleolus).

It is preferable for at least one amino acid residue of the neuronal differentiation-inducing peptide provided by this invention to be amidated. By amidating the carboxyl group of an amino acid residue (typically, the C-terminal amino acid residue on the peptide chain), the structural stability (e.g., the protease resistance) of the neuronal differentiation-inducing peptide can be enhanced.

In the neuronal differentiation-inducing peptide, it is desirable for the total number of amino acid residues making up the peptide chain to be 100 or less, and preferably 50 or less. The chemical synthesis of such peptides having a short chain length is easy, enabling neuronal differentiation-inducing peptides to be readily provided. The conformation of the peptide is not subject to any particular limitation, so long as the peptide exhibits a neuronal differentiation-inducing ability in the environment in which it is used. However, a straight-chain or helical configuration is preferred because the peptide does not readily become an immunogen (antigen). A peptide having such a shape does not readily form an epitope. From such a standpoint, straight-chain and relatively low-molecular-weight (typically having a number of amino acid residues of 50 or less (especially 40 or less)) peptides are preferred as neuronal differentiation-inducing peptides suitable for a neuronal differentiation inducer.

It is desirable for the APP signal peptide-related sequence to account for a proportion of the entire amino acid sequence (i.e., the number of amino acid residues constituting the APP signal peptide-related sequence portion, as a percentage of the total number of amino acid residues constituting the peptide chain) which, although not subject to any particular limitation so long as the neuronal differentiation-inducing activity is not lost, is at least 20%, and preferably from 30 to 50%. The neuronal differentiation-inducing peptide of the invention is preferably such that all the amino acid residues are L-type amino acids. However, to the extent that the neuronal differentiation-inducing activity is not lost, some or all of the amino acid residues may be substituted with D-type amino acids.

Insofar as the neuronal differentiation-inducing activity is not lost, the neuronal differentiation-inducing peptide of the invention may include in portions thereof sequences which cannot be included in the APP signal peptide-related sequences and the nucleolar localization signal-related sequences. Although not subject to any particular limitation, sequences which are able to retain the three-dimensional shape (typically, the straight-chain shape) of the APP signal peptide-related sequence portion in the peptide chain are preferred as such partial sequences. An illustrative example is a linker sequence (hinge region) which links together an APP signal peptide-related sequence portion and a nucleolar localization signal-related sequence portion. Typical examples of such linker sequences include those composed of about one to nine (e.g., one, two or three) glycine residues and/or serine residues (see the subsequently described working examples).

Of the neuronal differentiation-inducing peptides disclosed herein, those having a relatively short peptide chain can easily be produced according to a common chemical synthesis process. For example, use may be made of a known solid-phase synthesis process or liquid-phase synthesis process. A solid-phase synthesis process which employs t-butyloxycarbonyl (Boc) or 9-fluorenylmethoxycarbonyl (Fmoc) as the amino group-protecting group is preferred.

The neuronal differentiation-inducing peptide having a number of amino acid residues of 100 or less (especially 50 or less) disclosed herein can easily be synthesized as a peptide chain having the desired amino acid sequence and modifying (e.g., C-terminal amidating) portions by a solid-phase synthesis process using a commercial peptide synthesizer (available from, for example, Intavis AG or Applied Biosystems).

Alternatively, the neuronal differentiation-inducing peptide may be biosynthesized by a genetic engineering technique. This approach is preferred in cases where a polypeptide having a relatively long peptide chain is produced. That is, the DNA of a nucleotide sequence (including the ATG initiation codon) which codes for the amino acid sequence of the desired neuronal differentiating-inducing peptide is synthesized. Then, a recombinant vector having an expression gene construct composed of this DNA and various regulatory elements (including promoters, ribosome binding sites, terminators, enhancers, and various cis-elements which control the expression level) for expressing this amino acid sequence within a host cell is constructed in accordance with the host cell.

Using an ordinary technique, this recombinant vector is inserted into given host cells (e.g., yeasts, insect cells, plant cells, mammalian cells), and the host cells or tissue or individuals containing those cells are cultured under specific conditions. In this way, the target polypeptide can be expressed and produced intracellularly. Next, by isolating from the host cells (when the polypeptide is secreted, from within the culture medium) and purifying the polypeptide, the target neuronal differentiation-inducing peptide can be obtained.

Methods hitherto used in the art may be directly employed without modification as the method of constructing the recombinant vector and the method for introducing the constructed recombinant vector into a host cell. Because such methods themselves are not distinctive to the present invention, detailed explanations are omitted here.

For example, a fused protein expression system may be employed for efficient large-volume production within host cells. That is, a gene (DNA) coding for the amino acid sequence of the target neuronal differentiation-inducing peptide is chemically synthesized, and the synthesized gene is introduced to a preferred site on a suitable fused protein expression vector (a glutathione S-transferase (GST) fused protein expression vector such as the pET series available from Novagen and the pGEX series available from Amersham Bioscience). The host cells (typically, *Escherichia coli*) are then transformed by the vector. The resulting transformant is cultured, thereby producing the target fused protein. This protein is then extracted and purified. Next, the purified fused protein thus obtained is cleaved with a specific enzyme (protease), and the liberated target peptide fragments (the designed neuronal differentiation-inducing peptide) are recovered by a method such as affinity chromatography. The neuronal differentiation-inducing peptide of the invention may be produced by using such a conventional, known fused protein expression system (e.g., the GST/His system available from Amersham Bioscience may be used).

Alternatively, the target polypeptide may be synthesized in vitro by constructing template DNA for an acellular protein synthesis system (i.e., a synthesized gene fragment having a nucleotide sequence which codes for the amino acid sequence of the neuronal differentiation-inducing peptide) and, using the various compounds required for peptide synthesis (e.g., ATP, RNA polymerase, amino acids), employing an acellular protein synthesis system. For information concerning acellular protein synthesis systems, reference may be made to, for example, Shimizu et al., *Nature Biotechnology*, 19, 751-755 (2001), and Madin et al., *Proc. Natl. Acad. Sci. USA*, 97(2), 559-564 (2000). Based on the technology described in these articles, many corporations had already carried out the commissioned production of polypeptides at the time this application was filed. Also, PROTEIOS™, a wheat germ cell-free protein synthesis kit available from Toyobo Co., Ltd. (Japan), is commercially available.

Therefore, as mentioned above, once the amino acid sequence (APP signal peptide-related sequence) to be used has been determined and the peptide chain has been designed, the target neuronal differentiation-inducing peptide can easily be synthesized and produced by an acellular protein synthesis system in accordance with the amino acid sequence. For example, the neuronal differentiation-inducing peptide of the invention can be easily produced based on the Puresystem® from Post Genome Institute Co., Ltd.

A single-strand or double-strand polynucleotide containing a nucleotide sequence coding for the neuronal differentiation-inducing peptide disclosed herein and/or a nucleotide sequence complementary thereto can easily be produced (synthesized) by a hitherto known method. That is, by selecting codons corresponding to the respective amino acid residues making up the designed amino acid sequence, the nucleotide sequence corresponding to the amino acid sequence of the neuronal differentiation-inducing peptide is easily determined and provided. Then, once the nucleotide sequence has been determined, using a DNA synthesizer or the like, a polynucleotide (single-strand) corresponding to the desired nucleotide sequence can easily be obtained. In addition, using the resulting single-strand DNA as the template, the target double-strand DNA can be obtained using various enzymatic means of synthesis (typically, PCR).

The polynucleotide provided by the invention may be in the form of DNA or in the form of RNA (e.g., mRNA). The DNA may be provided as double-stranded DNA or as single-stranded DNA. When provided as a single strand, it may be either a coding strand (sense strand) or an anticoding strand (antisense strand) which is the sequence complementary thereto.

The polynucleotide provided by the invention may, as described above, be used as a material for constructing a recombinant gene (expression cassette) for producing the neuronal differentiation-inducing peptide, either in various host cells or in an acellular protein synthesis system.

According to the invention, there is provided a polynucleotide having a nucleotide sequence which codes for a neuronal differentiation-inducing peptide having a novel amino acid sequence and/or a nucleotide sequence complementary to such a sequence. For example, artificially designed polynucleotides which include (or are substantially composed of) nucleotide sequences coding for the respective amino acid sequences of SEQ ID NOS: 1 to 35 in which the total number of amino acid residues making up the peptide chain is 50 or less (preferably 40 or less), and/or nucleotide sequences complementary thereto, are provided.

Preferred neuronal differentiation-inducing peptides of the invention have a high neuronal differentiation-inducing activity on at least one type of cell. For this reason, they can be advantageously used as the active ingredient in a neuronal differentiation inducer. The neuronal differentiation-inducing peptide included in the neuronal differentiation inducer may be in the form of a salt, provided there is no loss in the neuronal differentiation-inducing activity. For example, use may be made of an acid addition salt of the peptide, which may be obtained by subjecting a commonly used inorganic acid or organic acid to an addition reaction according to a conventional method. Alternatively, use may be made of other salts (e.g., metal salts), provided they have neuronal differentiation-inducing activities.

The neuronal differentiation inducer may also include, apart from the neuronal differentiation-inducing peptide serving as the active ingredient, various carriers that are medically (pharmaceutically) acceptable for the mode of use. Carriers that are generally used in peptide medications as diluents, excipients or the like are preferred. Although these may suitably differ according to the use and form of the neuronal differentiating inducer, typical examples include water, physiological buffers and various organic solvents. The carrier may be an aqueous solution containing a suitable concentration of an alcohol (e.g., ethanol), glycerol, or a non-drying oil such as olive oil. Alternatively, the carrier may be liposomes. Examples of secondary ingredients that may be included in the neuronal differentiation inducer include various fillers, thickeners, binders, wetting agents, surfactants, dyes and fragrances.

The form of the neuronal differentiating inducer is not subject to any particular limitation. Examples of typical forms include liquid preparations, suspensions, emulsions, aerosols, foams, pellets, powders, tablets, capsules and ointments. For use in injection or the like, the neuronal differentiating inducer may be rendered into a freeze-dried form or granules for preparing a drug solution by dissolution in physiological saline or a suitable buffer (e.g., PBS) just prior to use.

The process of preparing a drug (composition) in various forms by using as the materials the neuronal differentiation-inducing peptide (main ingredient) and various carriers (secondary ingredients) may itself be in general accordance with a conventional known method. Because such preparation processes themselves are not distinctive to the present invention, detailed descriptions are omitted here. An example of a detailed information source relating to formulation is *Comprehensive Medicinal Chemistry*, edited by Corwin Hansch and published by Pergamon Press (1990). The entire contents of this book are incorporated herein by reference.

The neuronal differentiation inducer furnished by the present invention may be used in a manner and dose that accords with the form thereof and the intended purpose.

For example, the neuronal differentiation-inducing peptide containing the APP signal peptide-related sequence disclosed herein (i.e., the neuronal differentiation inducer containing this peptide) may be administered as a liquid preparation to the patient (i.e., in vivo) in exactly the desired amount by intravenous, intramuscular, hypodermal, intradermal or intraperitoneal injection. Alternatively, this neuronal differentiation-inducing peptide may be administered orally in a solid form such as tablets. In this way, nerve cells can be generated (produced) from somatic stem cells present within the living organism, typically at or near the site of disease. This makes it possible to effectively treat various neurological disorders for which nerve regeneration is an important mode of treatment. For example, the treatment of neurological disorders such as Alzheimer disease, Parkinson disease, cerebral infarction, paralysis of the body due to spinal cord injury, cerebral contusions, amyotrophic lateral sclerosis, Huntington disease, brain tumors and retinal degeneration by a regenerative medical approach is achieved.

Alternatively, by administering a suitable amount of a neuronal differentiation inducer (neuronal differentiation-inducing peptide) to a cellular material temporarily or permanently removed from a living organism, that is, to living tissue or a cell mass (e.g., a somatic stem cell culture), nerve cells can be efficiently generated in vitro. This means that the desired nerve cells can be produced in a large quantity within such cellular material.

Moreover, even when the nerve cells that have been produced in a large quantity, or cellular material (living tissue or cell mass) containing these produced nerve cells, are returned again to the living organism (typically, at the site of disease where neuronal regeneration is required), therapeutic effects similar to those obtained when a neuronal differentiation inducer (neuronal differentiation-inducing peptide) is administered directly in vivo are achievable.

As is apparent from the above explanation, this invention is also able to provide cells, cell masses or living tissue in which differentiation to nerve cells useful in the treatment of neurological disorders has been induced by using one of the neuronal differentiation-inducing peptides disclosed herein.

Also, polynucleotides coding for the neuronal differentiation-inducing peptides of the invention may be used as materials employed in so-called gene therapy. For example, by integrating a gene (typically, a DNA segment or a RNA segment) coding for a neuronal differentiation-inducing peptide into a suitable vector and inserting the vector at the target site, it is possible to continuously express the neuronal differentiation-inducing peptide of the present invention within a living organism (cell). Therefore, polynucleotides (e.g., DNA segments, RNA segments) coding for the neuronal differentiation-inducing peptides of the present invention are useful as drugs for treating or preventing neurological disorders in the above types of patients.

Several examples of the invention are described below, although these examples are not intended to limit the scope of the invention.

EXAMPLE 1

Peptide Synthesis

The total of 15 types of peptides (Samples 1 to 15) shown in Table 1 were produced using the subsequently described peptide synthesizer. Table 1 shows the amino acid sequences and the total number of amino acid residues for each of the sample peptides.

Sample 1 and Sample 2 each have, nearer the N-terminal with respect to the glycine linker, a partial amino acid sequence selected from the APP signal peptide sequence shown in SEQ ID NO: 2.

That is, Sample 1 has, as the APP signal peptide-related sequence, an N-terminal side partial amino acid sequence composed of the total of 6 amino acid residues from the position 1 (N-terminal) methionine residue to the position 6 alanine residue, counting from the N-terminal amino acid residue of the signal peptide sequence of SEQ ID NO: 2.

Sample 2 has, as the APP signal peptide-related sequence, a C-terminal side partial amino acid sequence composed of the total of 11 amino acid residues from the position 7 leucine residue to the position 17 (C-terminal) alanine residue, counting from the N-terminal amino acid residue of the signal peptide sequence of SEQ ID NO: 2.

In addition, Sample 3 has, as the APP signal peptide-related sequence, the entire signal peptide sequence of SEQ ID NO: 3.

Samples 4 to 15 each have, on the N-terminal side from the glycine linker, a partial amino acid sequence selected from the APP signal peptide sequence shown in SEQ ID NO: 3.

That is, Sample 4 has, as the APP signal peptide-related sequence, a C-terminal side partial amino acid sequence composed of the total of 15 amino acid residues from the position 3 proline residue to the position 17 (C-terminal) alanine residue, counting from the N-terminal amino acid residue of the signal peptide sequence of SEQ ID NO: 3.

TABLE 1

| Sample No. | Amino acid sequence | Total number of amino acid residues |
|---|---|---|
| 1 | MLPGLAGKKRTLRKNDRKKR (SEQ ID NO: 30) | 20 |
| 2 | LLLLAAWTARAGKKRTLRKNDRKKR (SEQ ID NO: 10) | 25 |
| 3 | MLPSLALLLLAAWTVRAGKKRTLRKNDRKKR (SEQ ID NO: 17) | 31 |
| 4 | PSLALLLLAAWTVRAGKKRTLRKNDRKKR (SEQ ID NO: 19) | 29 |
| 5 | SLALLLLAAWTVRAGKKRTLRKNDRKKR (SEQ ID NO: 20) | 28 |
| 6 | LALLLLAAWTVRAGKKRTLRKNDRKKR (SEQ ID NO: 21) | 27 |
| 7 | ALLLLAAWTVRAGKKRTLRKNDRKKR (SEQ ID NO: 22) | 26 |
| 8 | LLLLAAWTVRAGKKRTLRKNDRKKR (SEQ ID NO: 23) | 25 |
| 9 | LLLAAWTVRAGKKRTLRKNDRKKR (SEQ ID NO: 24) | 24 |
| 10 | LLAAWTVRAGKKRTLRKNDRKKR (SEQ ID NO: 25) | 23 |
| 11 | LAAWTVRAGKKRTLRKNDRKKR (SEQ ID NO: 26) | 22 |
| 12 | AAWTVRAGKKRTLRKNDRKKR (SEQ ID NO: 27) | 21 |
| 13 | AWTVRAGKKRTLRKNDRKKR (SEQ ID NO: 28) | 20 |
| 14 | WTVRAGKKRTLRKNDRKKR (SEQ ID NO: 29) | 19 |
| 15 | LLLLAAGKKRTLRKNDRKKR (SEQ ID NO: 32) | 20 |

As shown in Table 1, each sample peptide is a chemically synthesized straight-chain peptide constituted so as to include on the C-terminal side of the peptide chain the nucleolar localization signal-related sequence shown in SEQ ID NO: 1 and to include on the N-terminal side thereof, after an intervening linker composed of one glycine residue, an amino acid sequence derived from the APP signal peptide shown in SEQ ID NO: 2 or SEQ ID NO: 3, and is composed of from 19 to 31 amino acid residues in all.

Sample 5 has, as the APP signal peptide-related sequence, a C-terminal side partial amino acid sequence composed of the total of 14 amino acid residues from the position 4 serine residue to the position 17 (C-terminal) alanine residue, counting from the N-terminal amino acid residue of the signal peptide sequence of SEQ ID NO: 3.

Sample 6 has, as the APP signal peptide-related sequence, a C-terminal side partial amino acid sequence composed of the total of 13 amino acid residues from the position 5 leucine residue to the position 17 (C-terminal) alanine residue, counting from the N-terminal amino acid residue of the signal peptide sequence of SEQ ID NO: 3.

Sample 7 has, as the APP signal peptide-related sequence, a C-terminal side partial amino acid sequence composed of the total of 12 amino acid residues from the position 6 alanine residue to the position 17 (C-terminal) alanine residue, counting from the N-terminal amino acid residue of the signal peptide sequence of SEQ ID NO: 3.

Sample 8 has, as the APP signal peptide-related sequence, a C-terminal side partial amino acid sequence composed of the total of 11 amino acid residues from the position 7 leucine residue to the position 17 (C-terminal) alanine residue, counting from the N-terminal amino acid residue of the signal peptide sequence of SEQ ID NO: 3.

Sample 9 has, as the APP signal peptide-related sequence, a C-terminal side partial amino acid sequence composed of the total of 10 amino acid residues from the position 8 leucine residue to the position 17 (C-terminal) alanine residue, counting from the N-terminal amino acid residue of the signal peptide sequence of SEQ ID NO: 3.

Sample 10 has, as the APP signal peptide-related sequence, a C-terminal side partial amino acid sequence composed of the total of 9 amino acid residues from the position 9 leucine residue to the position 17 (C-terminal) alanine residue, counting from the N-terminal amino acid residue of the signal peptide sequence of SEQ ID NO: 3.

Sample 11 has, as the APP signal peptide-related sequence, a C-terminal side partial amino acid sequence composed of the total of 8 amino acid residues from the position 10 leucine residue to the position 17 (C-terminal) alanine residue, counting from the N-terminal amino acid residue of the signal peptide sequence of SEQ ID NO: 3.

Sample 12 has, as the APP signal peptide-related sequence, a C-terminal side partial amino acid sequence composed of the total of 7 amino acid residues from the position 11 alanine residue to the position 17 (C-terminal) alanine residue, counting from the N-terminal amino acid residue of the signal peptide sequence of SEQ ID NO: 3.

Sample 13 has, as the APP signal peptide-related sequence, a C-terminal side partial amino acid sequence composed of the total of 6 amino acid residues from the position 12 alanine residue to the position 17 (C-terminal) alanine residue, counting from the N-terminal amino acid residue of the signal peptide sequence of SEQ ID NO: 3.

Sample 14 has, as the APP signal peptide-related sequence, a C-terminal side partial amino acid sequence composed of the total of 5 amino acid residues from the position 13 tryptophan residue to the position 17 (C-terminal) alanine residue, counting from the N-terminal amino acid residue of the signal peptide sequence of SEQ ID NO: 3.

By contrast, Sample 15 has an amino acid sequence composed of the total of 6 amino acid residues from the position 7 leucine residue to the position 12 alanine residue, counting from the N-terminal amino acid residue of the signal peptide sequence of SEQ ID NO: 3. That is, Sample 15 does not correspond to either the above-described N-terminal side partial amino acid sequence or the above-described C-terminal side partial amino acid sequence defined in the specification. Hence, Sample 15 is a peptide which does not have the APP signal peptide-related sequence defined in the specification.

Each of the above peptides was synthesized by a solid-phase synthesis process (Fmoc process) using a commercial peptide synthesizer (MultiPep RS, a product of Intavis AG). HATU (O-(7-azabenzotriazol-1-yl)-1,1,3,3-tetramethyluronioum hexafluorophosphate, a product of Watanabe Chemical Industries, Ltd.) and DIEA (diisopropylethylamine, a product of Wako Pure Chemical Industries, Ltd.) were used as the condensing agents, and the resins and amino acids used in the solid-phase synthesis process were procured from NOVA Biochem. In cases where the C-terminus of the amino acid sequence is amidated, Rink Amide resin (100 to 200 mesh) may be used as the solid-phase support. However, this was not used in the working examples here.

The deprotection reaction and condensation reaction were repeatedly carried out in accordance with the synthesis program of the peptide synthesizer, thereby elongating the peptide from the Fmoc-amino acid which bonds to the resin so as to obtain a synthesized peptide of the intended chain length. Specifically, the operations of cleaving and removing the Fmoc group serving as the amino protecting group on the amino acid with 20% piperidine/dimethylformamide (DMF) (peptide synthesis grade, a product of Wako Pure Chemical Industries), washing with DMF, reacting with 4 equivalents each of Fmoc-amino acid (—OH) and washing with DMF were repeated. After the peptide chain elongation reactions were entirely completed, the Fmoc group was cleaved with 20% piperidine/DMF, and the reaction product was washed, first with DMF, then with ethanol.

Following solid-phase synthesis, the synthesized peptide chain was transferred together with the resin to a centrifuge tube, 1.8 mL of ethanediol, 0.6 mL of m-cresol, 3.6 mL of thioanisole and 24 mL of trifluoroacetic acid were added, and the mixture was stirred at room temperature for 2 hours. The resin that had been bonded to the peptide chain was then removed by filtration.

Next, cold diethyl ether was added to the filtrate and cooling was carried out with ice-cooled water to give a peptide precipitate. The supernatant was then discarded by centrifugal separation (5 minutes at 2500 rpm). Cold diethyl ether was freshly added to the precipitate, which was thoroughly stirred, following which centrifugal separation was carried out under the same conditions as above. This stirring and centrifugal separation treatment were repeated a total of three times.

The resulting peptide precipitate was dried in vacuo, and purification was carried out using a high-performance liquid chromatograph (Waters 600, a product of Waters Corporation).

Specifically, using a precolumn (Guard-Pak Delta-pak C18 A300, a product of Nihon Waters K.K.) and a C18 reversed-phase column (XTerra® column, a product of Nihon Waters K.K.; MS C18, 5 μm, 4.6×250 mm), a mixture of 0.1% trifluoroacetic acid in water and 0.1% trifluoroacetic acid in acetonitrile was used as the eluant. That is, while increasing over time the amount of the above acetonitrile solution of trifluoroacetic acid included in the eluant (in terms of the volumetric ratio, providing a concentration gradient of from 10% to 80%), separation and purification were carried out for 30 to 40 minutes using the above column at a flow rate of 1.5 mL/min. The peptide which eluted from the reversed-phase column was detected at a wavelength of 220 nm using an ultraviolet detector (490E Detector, a product of Waters Corporation), and indicated as a peak on a recording chart.

In addition, the molecular weights of each of the eluted peptides were determined based on matrix-assisted laser desorption time of flight mass spectrometry (MALDI-TOF/MS) using the Voyager DE RP™ manufactured by PerSeptive Biosystems. As a result, the target peptide was confirmed to have been synthesized and purified.

EXAMPLE 2

Evaluation of Neuronal Differentiation-Inducing Activities of Synthesized Peptides The neuronal differentiation-inducing activities of the synthesized peptides obtained in Example 1 (Samples 1 to 15) were examined.

That is, the sample peptide was added to a culture broth of neuronal stem cells collected from a mouse (mouse neuronal stem cell growth medium, a product of Cell Applications), and incubated. Addition was carried out to a concentration of 0.5 µM for each peptide.

Next, once 7 days had elapsed following peptide addition, each of the cultured cells was nuclear stained with DAPI (4',6-diamidino-2-phenylindole) and examined with a fluorescence microscope. In addition, evaluation with a neuronal differentiation induction marker was carried out on the same samples. That is, using tubulin (specifically, β3-tubulin) as the marker for identifying neurons (nerve cells), the presence of tubulin (i.e., the presence or absence of neurons) within the culture solution was checked by a fluorescence antibody method using a fluorochrome-labeled anti-tubulin antibody for tubulin identification. The results are shown in FIGS. 1 to 15. The number of each figure corresponds to the number of the sample peptide used.

Each of these figures is a fluorescence micrograph (image) obtained by examining the state of neuronal differentiation by mouse neuronal stem cells following addition of the respective sample peptides and 7 days of culturing. The image was prepared by merging a DIC image, a DAPI nuclear stain image, and a fluorescence image showing the results of an investigation by an immune antibody method using fluorochrome-labeled anti-tubulin antibody.

Figure 16:
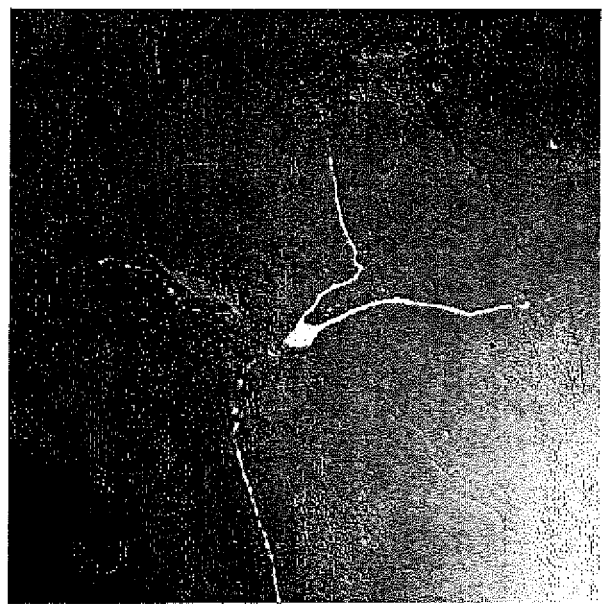
FIG. 16 is a fluorescence micrograph (image) obtained by culturing mouse neuronal stem cells in a neuronal differentiation culture (to which a neuronal differentiation-inducing peptide was not added) for 7 days, then examining the state of the cultured cells; the image was prepared by merging a differential interference contrast (DIC) image, a DAPI nuclear stain image, and a fluorescence image showing the results of an investigation by an immune antibody method using fluorochrome-labeled anti-tubulin antibody.

As a positive control, mouse neuronal stem cells were cultured in a mouse neuronal stem cell differentiation medium (product of Cell Applications) without adding any of the peptides. When 7 days had elapsed following the start of culturing, treatment and fluorescence microscopic examination were carried out in the same way as described above. The results are shown in FIG. 16.

Figure 17:
FIG. 17 is a fluorescence micrograph (image) obtained by culturing mouse neuronal stem cells in an ordinary growth culture (to which a neuronal differentiation-inducing peptide was not added) for 7 days, then examining the state of the cultured cells; the image was prepared by merging a differential interference contrast (DIC) image, a DAPI nuclear stain image, and a fluorescence image showing the results of an investigation by an immune antibody method using fluorochrome-labeled anti-tubulin antibody.

As a negative control, mouse neuronal stem cells were cultured in a mouse neuronal stem cell differentiation growth medium (product of Cell Applications) without adding any of the peptides. When 7 days had elapsed following the start of culturing, treatment and fluorescence microscopic examination were carried out in the same way as described above. The results are shown in FIG. 17.

As a result of the above evaluation tests, pronounced neuronal differentiation equal to or greater than the positive control (FIG. 16) was observed when the artificial peptides of Samples 1 to 14 (neuronal differentiation-inducing peptides) were added (see FIGS. 1 to 14). That is, even in cases where the peptides of any of Samples 1 to 14 were added, fluorescence due to the presence of fluorochrome-labeled anti-tubulin antibody was clearly observed. Of these, the peptides of Samples 2, 6, 7 and 8 were observed to have particularly high neuronal differentiation-inducing activities. On the other hand, in a negative control using the same growth medium, such fluorescence (neuronal differentiation) was not observed (FIG. 17).

This indicates that the neuronal stem cells differentiate into neurons owing to addition of the sample peptides, and thus demonstrates the usefulness of the APP signal peptide as a peptide motif relating to neuronal differentiation induction.

EXAMPLE 3

Preparation of Granules

The Sample 1 peptide (50 mg), 50 mg of crystallized cellulose and 400 mg of lactose were mixed together, following which 1 mL of an ethanol/water mixture was added and kneading was carried out. The kneaded material was then granulated according to a conventional method, thereby giving granules (granular neuronal differentiation inducer) containing a neuronal differentiation-inducing peptide as the main ingredient.

INDUSTRIAL APPLICABILITY

As described above, the neuronal differentiation-inducing peptides of the invention have high neuronal differentiation-inducing activities, and thus can be employed as peptide ingredients for medicinal purposes.

SEQ ID NO: 1 to SEQ ID NO: 35: Synthetic peptides

The invention claimed is:

1. A composition for inducing neuronal differentiation of at least one type of stem cell into a nerve cell, the composition comprising:
an artificially synthesized peptide consisting of:
(A) a signal peptide in amyloid precursor protein (APP), or an N-terminal side partial amino acid sequence that is part of the amino acid sequence of the signal peptide and is composed of at least six consecutive amino acid residues counting from the N-terminal amino acid residue of the sequence, or a C-terminal side partial amino acid sequence that is part of the amino acid sequence of the signal peptide and is composed of at least five consecutive amino acid residues counting from the C-terminal amino acid residue of the sequence, wherein the signal peptide is the amino acid sequence of SEQ ID NO: 2 or SEQ ID NO: 3; and
(B) an amino acid sequence constituting a protein transduction domain, wherein the protein transduction domain is linked directly or via a linker sequence to (A) the signal peptide or the N-terminal side or C-terminal side partial amino acid sequence of the signal peptide, wherein the linker sequence is composed of one to nine glycine residues and/or serine residues; and
at least one pharmaceutically acceptable carrier.

2. The composition according to claim 1, wherein the protein transduction domain is composed of an amino acid sequence selected from SEQ ID NOS: 1 and 33-35.

3. The composition according to claim 2, wherein the protein transduction domain is linked, via the linker sequence, to (A) the signal peptide or the N-terminal side or C-terminal side partial amino acid sequence of the signal peptide.

4. The composition according to claim 1, wherein the artificially synthesized peptide includes (A) the signal peptide or the N-terminal side or C-terminal side partial amino acid sequence of the signal peptide on the N-terminal side of the protein transduction domain.

5. The composition according to claim 1, wherein the total number of amino acid residues constituting the artificially synthesized peptide is 50 or less.

6. The composition according to claim 1, wherein the artificially synthesized peptide consists of an amino acid sequence selected from SEQ ID NOS: 4-31.

7. The composition according to claim 1, wherein the stem cell is a neuronal stem cell.

8. An artificially synthesized peptide capable of inducing neuronal differentiation of at least one type of stem cell into a nerve cell, the artificially synthesized peptide consisting of:
(A) a signal peptide in amyloid precursor protein (APP), or an N-terminal side partial amino acid sequence that is part of the amino acid sequence of the signal peptide and is composed of at least six consecutive amino acid residues counting from the N-terminal amino acid residue of the sequence, or a C-terminal side partial amino acid sequence that is part of the amino acid sequence of the signal peptide and is composed of at least five consecutive amino acid residues counting from the C-terminal amino acid residue of the sequence, wherein the signal peptide is the amino acid sequence of SEQ ID NO: 2 or SEQ ID NO: 3; and (B) an amino acid sequence constituting a protein transduction domain, wherein the protein transduction domain is linked directly or via a linker sequence to (A) the signal peptide or the N-terminal side or C-terminal side partial amino acid sequence of the signal peptide, wherein the linker sequence is composed of one to nine glycine residues and/or serine residues.

9. The synthesized peptide according to claim 8, wherein the protein transduction domain is composed of an amino acid sequence selected from SEQ ID NOS: 1 and 33-35.

10. The synthesized peptide according to claim 9, wherein the protein transduction domain is linked, via the linker sequence, to (A) the signal peptide or the N-terminal side or C-terminal side partial amino acid sequence of the signal peptide.

11. The synthesized peptide according to claim 8, which includes (A) the signal peptide or the N-terminal side or C-terminal side partial amino acid sequence on the N-terminal side of the protein transduction domain.

12. The synthesized peptide according to claim 8, wherein the total number of amino acid residues constituting the synthesized peptide is 50 or less.

13. The synthesized peptide according to claim 8, which consists of an amino acid sequence selected from SEQ ID NOS: 4-31.

14. The synthesized peptide according to claim 8, wherein the stem cell is a neuronal stem cell.

* * * * *